United States Patent [19]

Ransom et al.

[11] Patent Number: 4,849,506
[45] Date of Patent: Jul. 18, 1989

[54] LEUKOREGULIN, AN ANTITUMOR LYMPHOKINE, AND ITS THERAPEUTIC USES

[75] Inventors: Janet H. Ransom, Germantown; Richard P. McCabe, Rockville; Martin V. Haspel, Silver Spring; Nicholas Pomato, Frederick, all of Md.

[73] Assignee: Akzo N.V., Arnhem, Netherlands

[21] Appl. No.: 906,353

[22] Filed: Sep. 11, 1986

Related U.S. Application Data

[63] Continuation-in-part of Ser. No. 721,060, Apr. 8, 1985, abandoned, Continuation-in-part of Ser. No. 600,303, Apr. 13, 1984, abandoned.

[51] Int. Cl.$^4$ .................. C07K 15/00; A61K 37/00
[52] U.S. Cl. ...................... 530/351; 530/350; 530/827; 435/68; 514/2; 514/8; 514/21; 424/85.1
[58] Field of Search .............. 530/350, 351, 827; 435/68; 514/2, 8, 21; 424/85.1

[56] References Cited

U.S. PATENT DOCUMENTS

| | | | |
|---|---|---|---|
| 4,613,459 | 9/1986 | Cantas et al. | 530/351 |
| 4,708,937 | 11/1987 | Remold | 530/351 |
| 4,708,948 | 11/1987 | Iwata et al. | 435/68 |
| 4,752,575 | 6/1988 | Gronyer et al. | 530/351 |
| 4,785,077 | 11/1988 | Kornbluth et al. | 530/351 |

OTHER PUBLICATIONS

Fuhrer et al. *J. Chromat* 248, 1982, p. 427.
Fuhrer et al., CA vol. 98, #119306t.
Harris et al., *J. Immunol* 126 (6) 1981, p. 2165.
Ransom et al., *Int. J. Cancer* 29, 1982, pp. 451–458.
Ransom et al., *Cancer Res.* 43, 1983, pp. 5222–5227.
Remold et al., *J. Immunol* 122(5) 1979, pp. 1920–1925.
Aggarwal, B. B., Moffat, B., and Harkins, R. N., "Human Lymphotoxin: Production by a Lymphoblastoid Cell Line, Purification and Initial Characterization", *J. Biol. Chem.*, 259:686–691, 1984.
Brouty-Boye, P. "Inhibitory Effects of Interferon on Cell Multiplication", *Lymphokine Reports*, 1:99–112, 1980.
Brown, R. L., Griffith, R. L., Neubauer, R. H., and Rabin, H., "The Effect of T-Cell Growth Factor on the Cell Cycle of Primate T Cells", *J. Immunol.*, 129:1849–1853, 1982.
DiPaolo, J. A., "Relative Difficulties in Transforming Human and Animal Cells in vitro", *J. Natl. Cancer Inst.*, 70:3–8, 1983.
Dolbeare, F. A., and Smith, R. E., "Flow Cytoenzymology: Rapid Enzyme Analysis of Single Cells", In, M. R. Melamid, P. F. Mullaney, and M. L. Mindelsohn (eds.), *Flow Cytometry and Sorting*, pp. 317–334, N.Y., John Wiley & Sons, 1979,
Evans, C. H., and DiPaolo, J. A., "Lymphotoxin: an Anticarcinogenic Lymphokine as Measured by Inhibition of Chemical Carcinogen or Ultraviolet-Irradiation-Induced Transformation of Syrian Hamster Cells", *Int. J. Cancer*, 27:45–49, 1981.
Evans, C. H. and Heinbaugh, J. A., "Lymphotoxin Cytotoxicity, a Combination of Cytolytic and Cytostatic Cellular Responses", *Immunopharmacology*, 3:347–359, 1981.
Evans, C. H., Heinbaugh, J. A., and DiPaolo, J. A., "Comparative Effectiveness of Lymphotoxin Anticarcinogenic and Tumor Cell Growth Inhibitory Activities", *Cell Immunol.*, 76:295–303, 1983.

(List continued on next page.)

*Primary Examiner*—Howard E. Schain
*Assistant Examiner*—Garnette D. Draper
*Attorney, Agent, or Firm*—Wiliam M. Blackstone

[57] ABSTRACT

Leukoregulin is identified, a biologically active lymphokine of molecular weight of about 120,000 to 140,000, with subunits of about 30,000 to 35,000, having the isoelectric focusing pH's of between 4.8 and 5.5 or between 7.5 and 8.3, which has the ability to regulate tumor cell physiology and growth without affecting the growth of normal cells. Methods for stimulating its production by monuclear cells, methods for its isolation and purification, and methods for its therapeutic uses are also disclosed.

3 Claims, 14 Drawing Sheets

OTHER PUBLICATIONS

Granger, G. A., and Kolb, W. P., "Lymphocyte in vitro Cytotoxicity: Mechanisms of Immune and Non-Immune Small Lymphocyte Mediated Target L Cell Destruction", *J. Immunol.*, 101:111–116, 1968.

Haspel, M. V., et al., *Science* 220:304–306, 1983.

Hoover, H. C., et al., *Cancer Res.*, Apr., 1984.

Kern, et al., *Int. J. Cancer*, 30:725–729, 1982.

Khan, A., et al., In *Human Lymphokines*, pp. 621–629, Academic Press, N.Y., 1982.

Kleinerman, E. S., Schroit, A. J., Fogler, W. E., and Fidler, I. J., "Tumoricidal Activation of Human Monocyte Activity in vitro by Free and Liposome Encapsulated Human Lymphokines", *J. Clin. Invest.*, 72:304–315, 1983.

Laemmli, V., *Nature*, 227:680–685, 1970.

Lambin, P., and Fine, J. M., *Anal Biochem.*, 98:160–168, 1979.

McConahey, P. J., and Dixon, F. J., *Int. Arch. Allergy Appl. Immunol.*, 29:185–189, 1966.

Mizel, S. B., Oppenheim, J. J., and Rosenstreich, D. L., "Characterization of Lymphocyte-Activating Factor Produced by the Macrophage Cell Line P388D1. I. Enhancement of LAF Production by Activated T Lymphocytes", *J. Immunol.*, 120:1497–1505, 1978.

Papermaster, B. W., et al., *In Lymphokines and Thymic Hormones*, Academic Press, N.Y., pp. 789–799.

Penn, I., "Depressed Immunity and the Development of Cancer", *Clinical Experimental Immunology*, 46:459, 1981.

Pross, H. F., Baines, M. G., Rubin, P., Shragge, P., and Patterson, M. S., "Spontaneous Human Lymphocyte-Mediated Cytotoxicity Against Tumor Target Cells. IX. The Quantitation of Natural Killer Cell Activity", *J. Clin. Immunol.*, 1:51–63, 1981.

Rabin, H., Hopkins, R. F., Ruscetti, F. W., Neubauer, R. H., Brown, R. L., and Kawakami, T. G., "Spontaneous Release of a Factor from a Continuous Line of Primate Tumor T Cells", *J. Immunol.*, 127:1852–1856, 1981.

Ransom, J. H. and Evans, C. H., "Lymphotoxin Enhances the Susceptibility of Neoplastic and Preneoplastic Cells to Natural Killer Cell Mediated Destruction", *Int. J. Cancer*, 29:451–458, 1982.

Ransom, J. H. and Evans, C. H., "Molecular and Biological Characterization of Syrian Hamster Lymphotoxin's Anticarcinogenic and Tumor Cell Growth Inhibitory Activities", *Cancer Res.*, 43:5222–5227, 1983.

Ransom, J. H., Evans, C. H., and DiPaolo, J. A., "Lymphotoxin Prevention of Diethylnitrosamine Carcinogenesis in vivo", *J. Natl. Cancer Inst.*, 69:741–744, 1982.

Ransom, J. H., Evans, C. H., Jones, A. E., Zoon, R. A., DiPaolo, J. A., "Control of the Carcinogenic Potential of $^{99m}$Technetium by the Immunologic Hormone Lymphotoxin", *Cancer Immunol. Immunother.*, 15:126–130, 1983.

Ransom, J. H., Pintus, C., and Evans, J. H. "Lymphotoxin Amplification of Tumor Cell Growth Inhibition is Specific for Natural Killer Cells but not for Macrophages", *Int. J. Cancer*, 32:93–97, 1983.

Ransom, J. H., Rundell, J. O., Heinbaugh, J. A., and Evans, C. H., "Biological and Physiocochemical Characterization of Keyhole Limpet Hemocyanin-Induced Guinea Pig Lymphotoxin", *Cell. Immunol.*, 67:1–13, 1982.

Remold, H. G., and Mednis, A. D., "Two Migration Inhibitory Factors Differ in Density and Susceptibility to Neuraminidase and Proteinases", *J. Immunol.*, 122:1920–1925, 1978.

Rosenberg, S. A., Henrichon, M. Coyne, J. A., and David, J. A., "In vitro Studies of LT Produced in Response to Antigen Stimulation of Lymphocytes", *J. Immunol*, 6:1623–1629, 1973.

Sawada, J., Shiori-Nakano, K., Osawa, T., "Cytotoxic Activity of Purified Guinea Pig Lymphotoxin Against Various Cell Lines", *Jpn. J. Exp. Med.*, 4:263–271, 1976.

Trinchieri, G., DeMarchi, M., Mayer, W., Savi, M., and Ceppelline, R., "Lymphocyte Antibody Lymphocytolytic Interaction (LALI) With Special Emphasis on HLA", *Transplant. Proc.*, 5:1631–1646, 1973.

Trinchieri, G., and Santoli, D., "Anti-Viral Activity Induced by Culturing Lymphocytes with Tumor-Derived or Virus-Transformed Cells", *J. Exp. Med.*, 147:1314–1333, 1978.

Williamson, B. D., Carswell, E. A., Rubin, B. Y., Prendergast, J. S., and Old, L. J., "Human Tumor Necrosis Factor Produced by Human B-Cell Lines: Synergistic Cytotoxic Interaction with Human Interferon", *Proc. Natl. Acad. Sci.*, 80:5397–5401, 1983.

Granger et al., Lymphokine Research, vol. 1, No. 2, pp. 45–49 (1982).

(List continued on next page.)

OTHER PUBLICATIONS

Ruddle et al., Lymphokine Research, vol. 2, No. 1, pp. 23-29 (1983).

Klostergaard et al., Molecular Immunology, vol. 18, No. 5, pp. 455-459, (1981).

Clinical Immunology and Immunopathology, vol. 5, pp. 31-47 (1976).

Weitzen et al., Cell Immunology, vol. 77, No. 1, (1983).

Harris et al., Journal of Immunology, vol. 126, No. 6, pp. 2165-2170, (1981).

Yamamoto et al., Journal of Biological Response Modifiers, vol. 3, No. 1 (1984).

British Pat. No. 2,108,528, Issued May 18, 1983, to Osawa et al.

European application No. 0,097,518, Issued Jan. 4, 1984 to Reinherz et al.

Gray et al., Nature, vol. 312, No. 20, pp. 720-724 (1984).

FIG. 12 CATION EXCHANGE CHROMATOGRAPHY
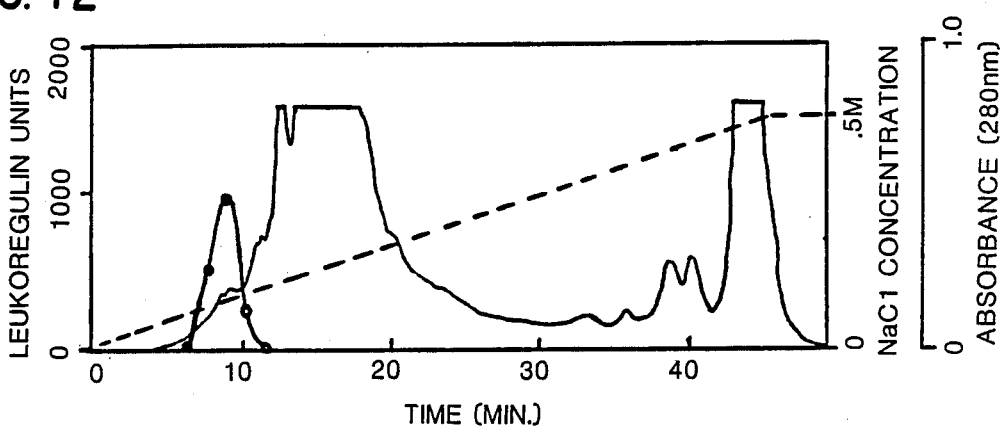
DEAE Anion Exchange
FIG. 9
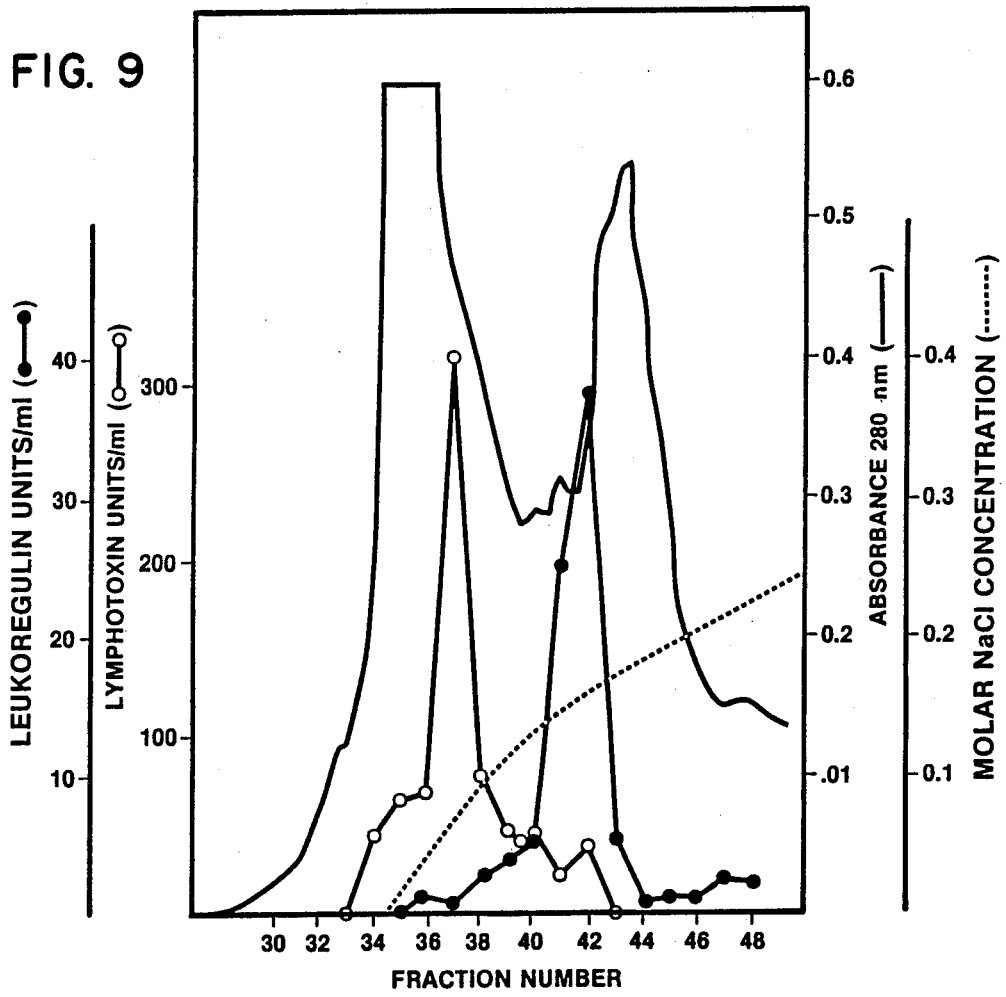

CLONING OF THE LEUKOREGULIN GENE $C_4$ REVERSE PHASE CHROMATOGRAPHY

LEUKOREGULIN, AN ANTITUMOR LYMPHOKINE, AND ITS THERAPEUTIC USES

This application is a continuation-in-part application of U.S. Ser. No. 06/721,060, filed Apr. 8, 1985, now abandoned which in turn is a continuation-in-part application of U.S. Ser. No. 06/600,303, filed Apr. 13, 1984 now abandoned.

This invention relates to our discovery of a new human lymphokine which is able to directly lyse and suppress the proliferation of human tumor cells, and to enhance their susceptibility to lysis mediated by natural killer lymphocytes. These antitumor activities have in the past been attributed to lymphotoxin. We have found, however, that human lymphokine preparations having these antitumor cell activities are biochemically separable from lymphotoxin and other previously isolated lymphokines, including interferon, interleukins 1 and 2, and macrophage activating factor activities.

BRIEF DESCRIPTION OF THE DRAWINGS

The FIGURES illustrate the identification of leukoregulin as a unique and previously unknown lymphokine and demonstrate its efficacy in controlling the growth of human tumor cells.

BACKGROUND OF THE INVENTION

Figure 2:
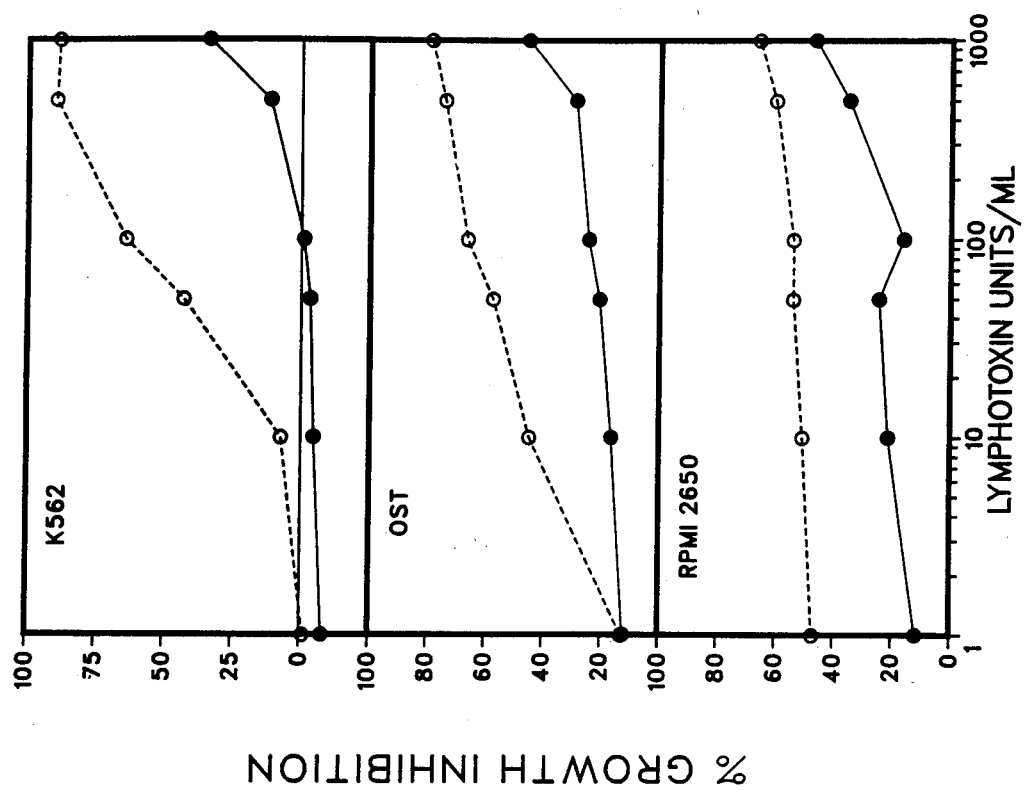
Figure 1:
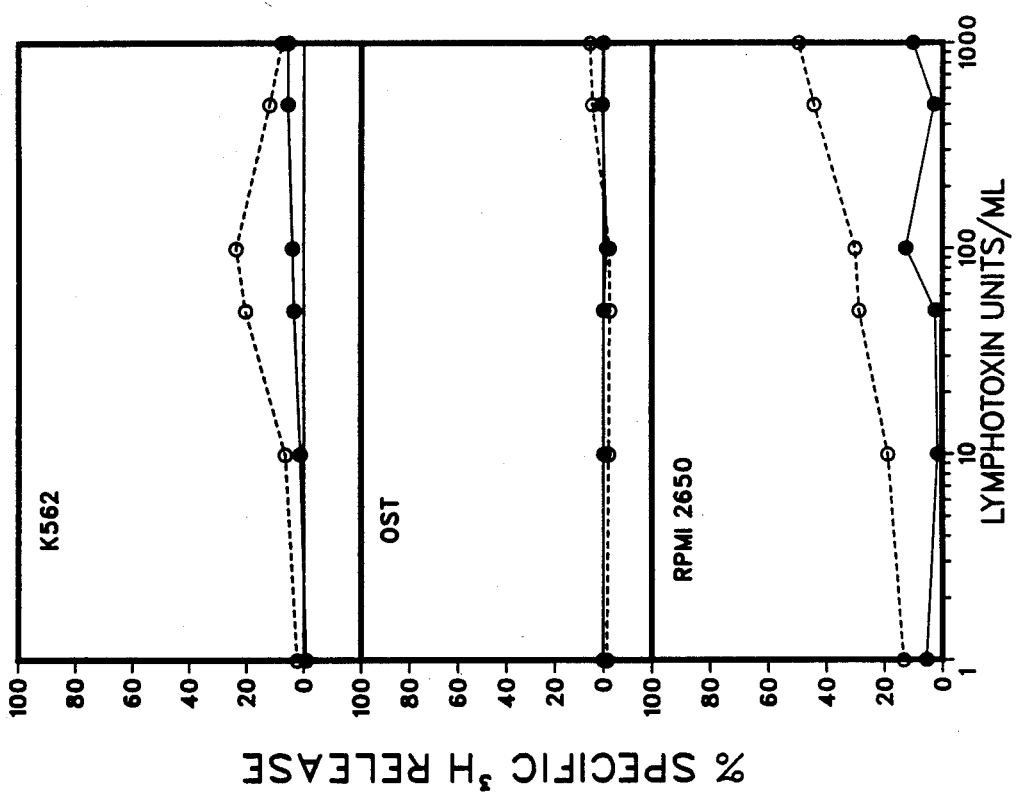
Figure 5:
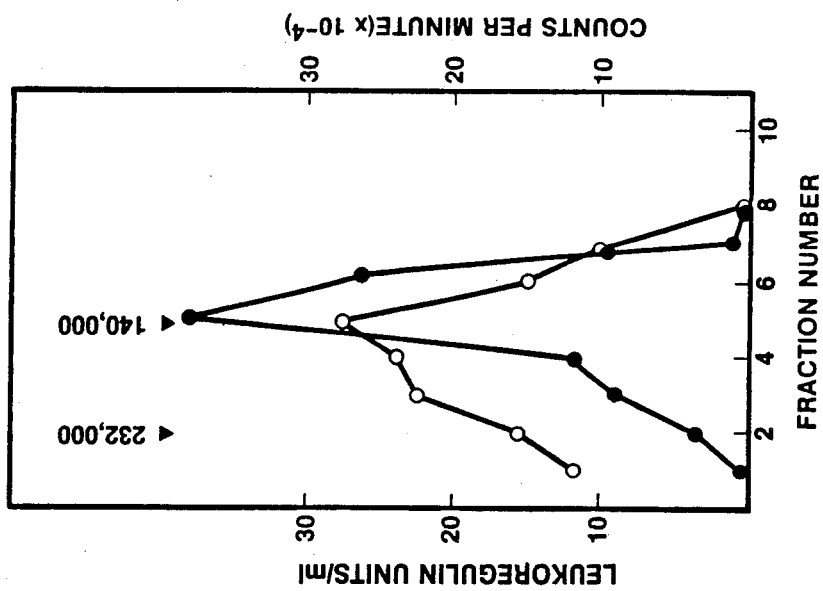
Figure 3:
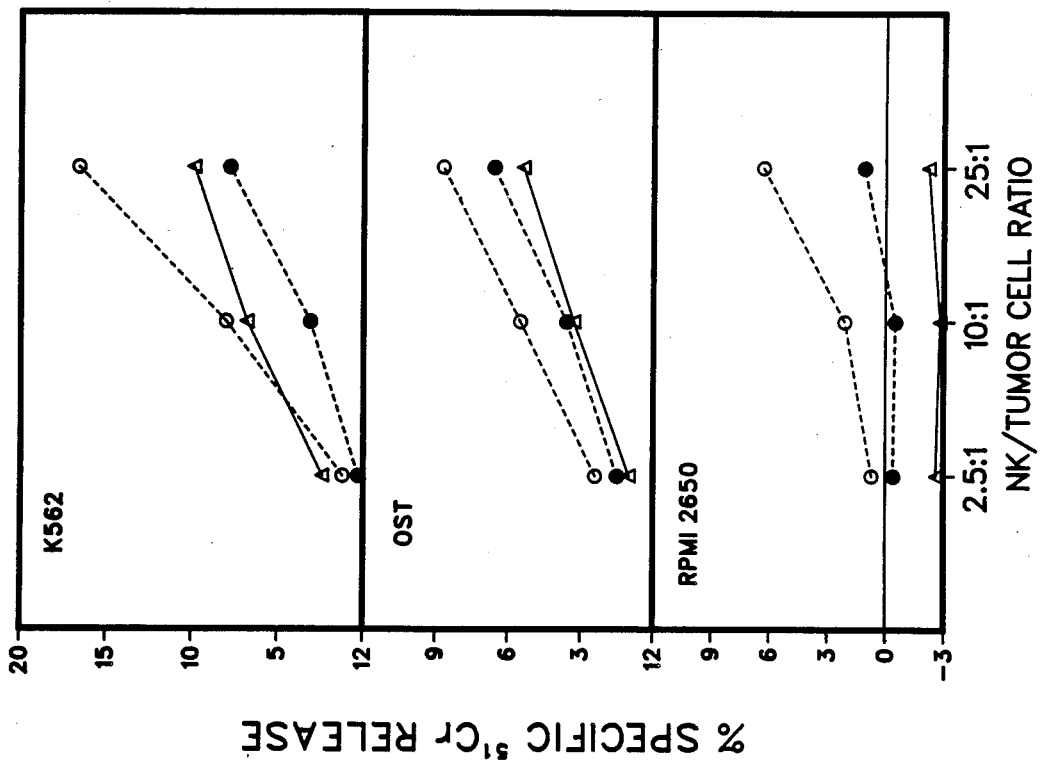
Figure 4:
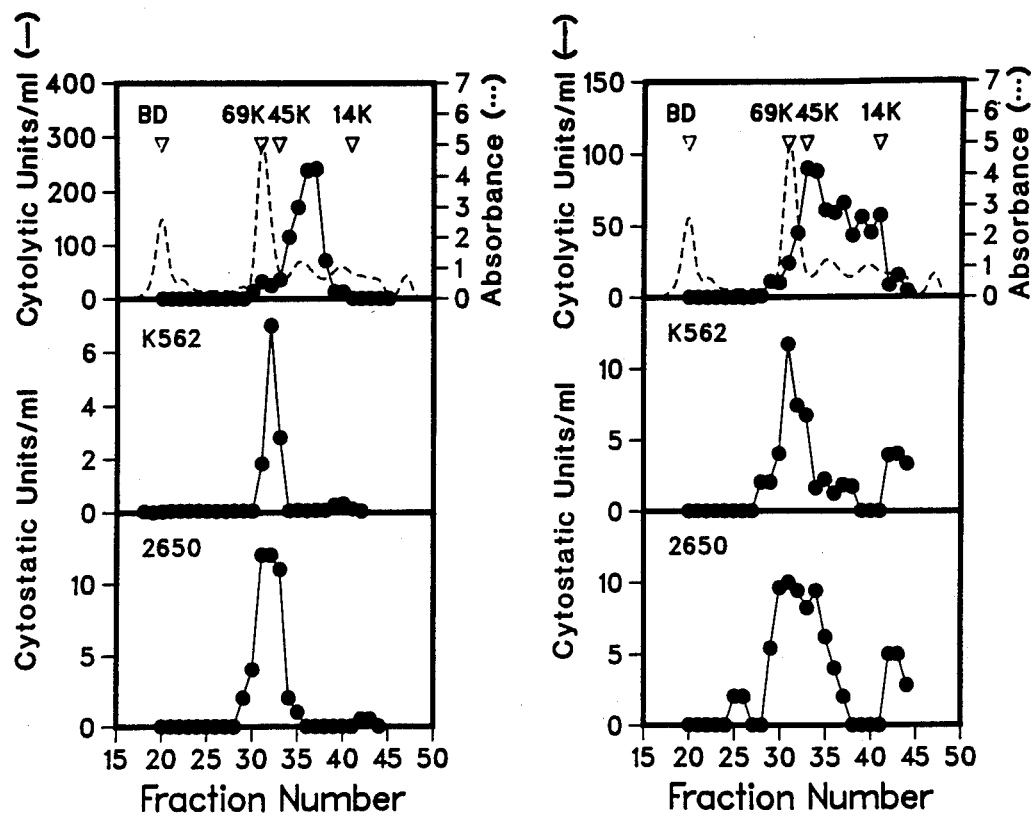
Figure 7:
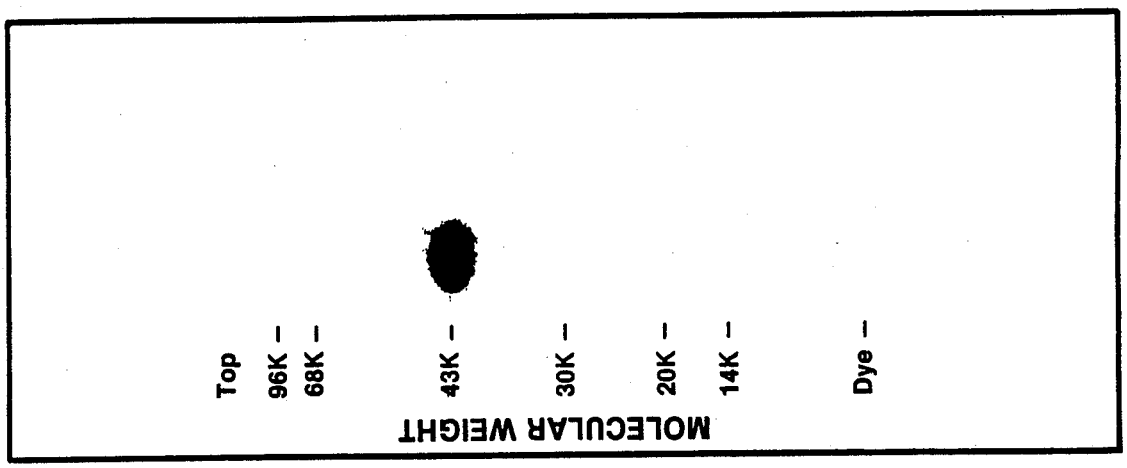
Figure 6:
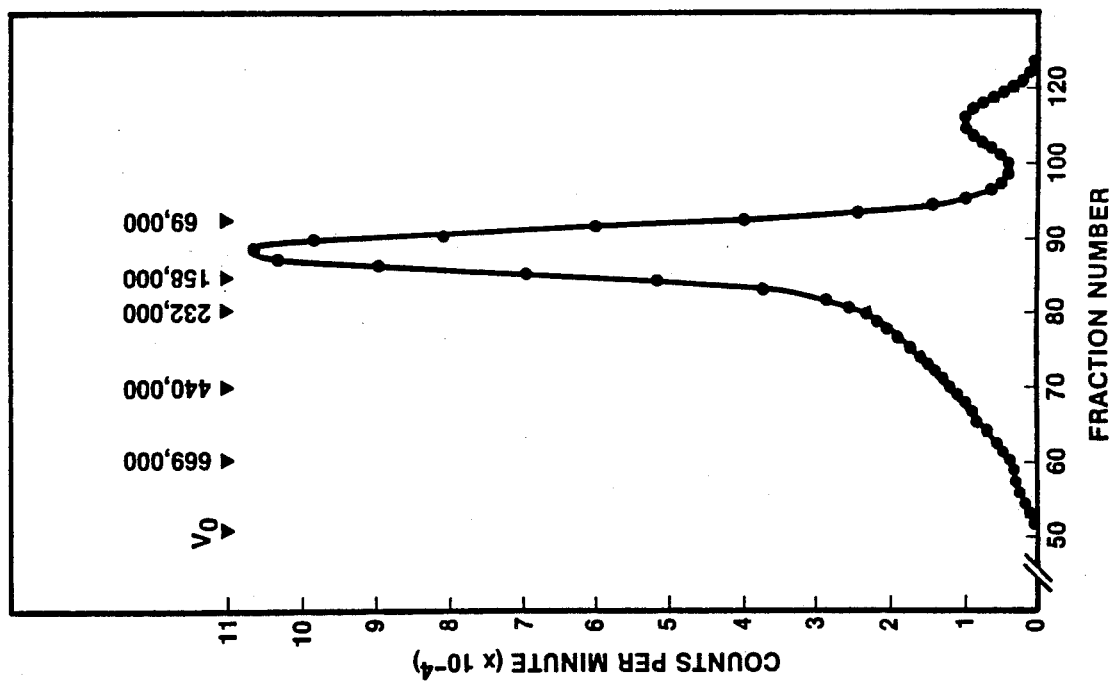
Figure 10:
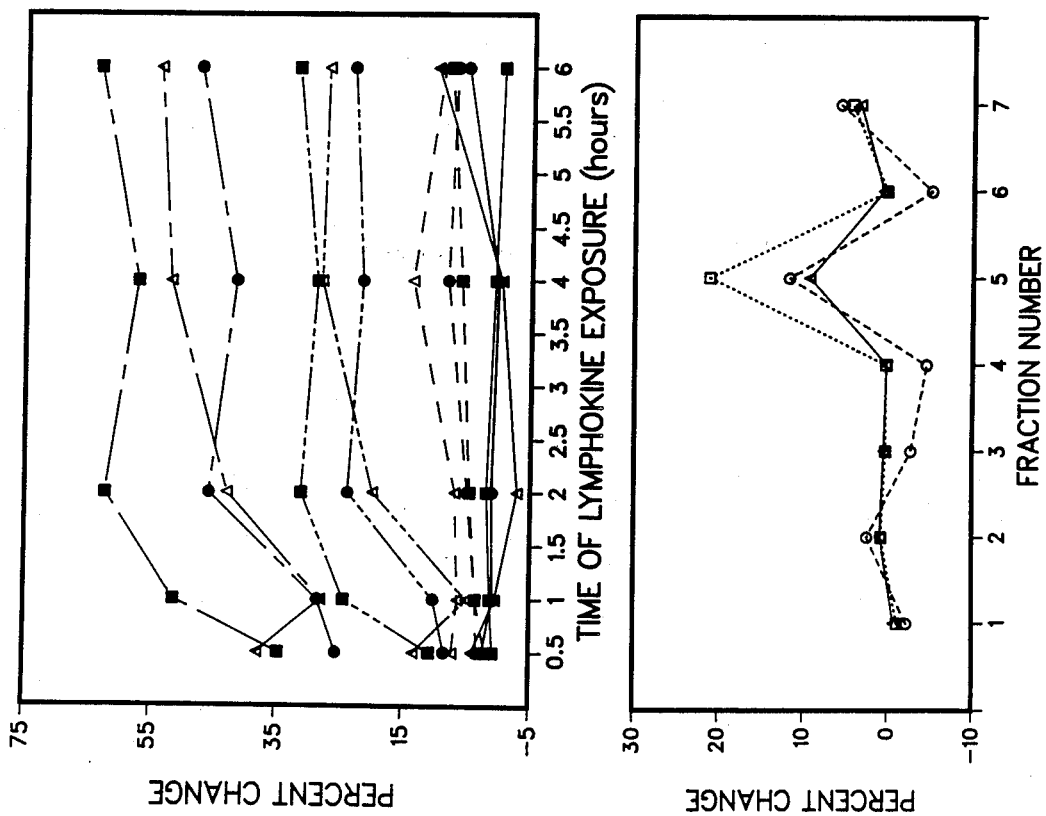
Figure 8:
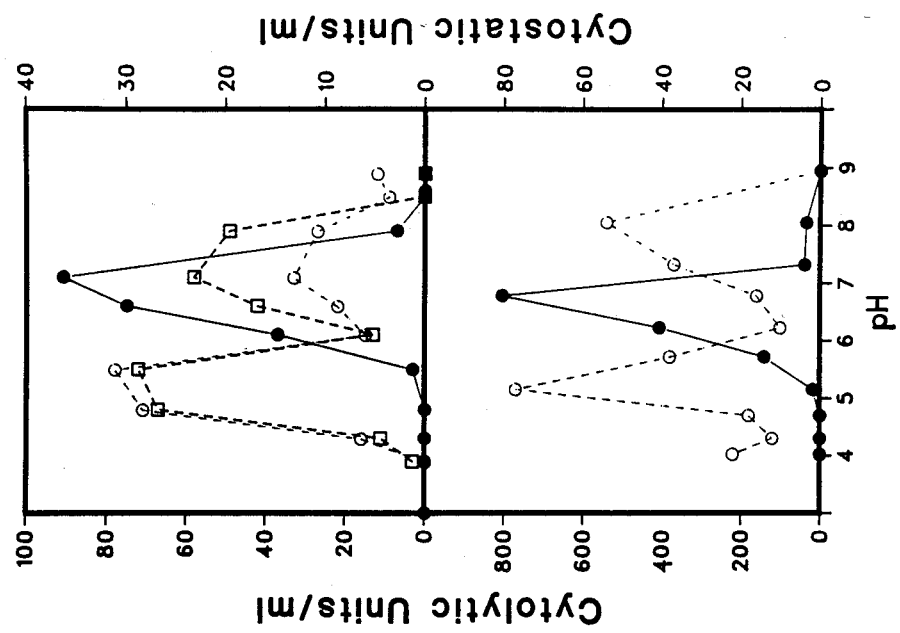
Figure 11:
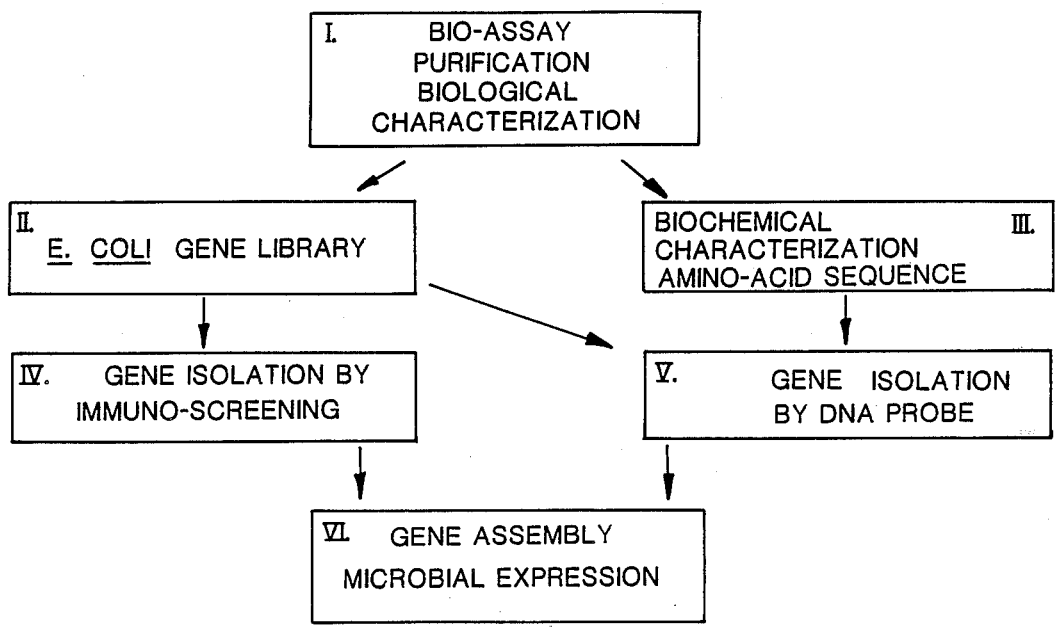

Lymphokines, the hormones of the immune system, have the potential to influence the development of cancer, to suppress the growth of tumorigenic cells, and even to destroy tumors. These hormones are glycoproteins, produced and secreted by certain types of lymphoid cells and targeted to interact with other specific cells. Particular lymphokines are known to be produced by and able to interact with more than one type of cell. Similarly, the activities of most lymphokines are known to be multifaceted; a particular lymphokine displaying inhibiting, stimulating, enhancing, contravening and other activities with respect to various target cells and conditions. Moreover, a particular lymphokine may act to both inhibit and enhance carcinogenesis under different circumstances. For example, interferon is known to inhibit viral carcinogenesis but enhance radiation carcinogenesis. Similarly, interferon exhibits the antagonistic activities of increasing the NK cell lysis of tumor cells, while increasing tumor cell resistance to NK cell activity; the former occurring earlier in time after exposure to interferon than the latter.

Lymphotoxin is a term introduced in 1968 to denote the soluble product of antigen or mitogen stimulated lymphocytes that mediate the cytolytic destruction of mouse L cells (9). Several laboratories subsequently demonstrated that lymphokine preparations containing lymphotoxin had direct-acting cytolytic and cytostatic activities against a variety of tumor cells (7,30,31), anti-carcinogenic activity toward cells undergoing neoplastic transformation (6,25,26), and the ability to enhance the sensitivity of preneoplastic and neoplastic cells to NK-mediated destruction (23,27).

An anticancer lymphokine in hamster lymphotoxin preparations distinct from that mediating mouse L cell cytolytic destruction was later identified on the basis of molecular charge (24). That 50,000 molecular weight molecule with an isoelectric pH of 5.0 was cytostatic for hamster tumor cells, did not inhibit the growth of normal hamster fetal fibroblasts, and inhibited the chemical and radiation-induced neoplastic transformation of hamster fetal cells, both in vitro and in vivo. The unique anti-cancer lymphokine was also identified as being distinct from interferon, interleukins 1 and 2, and macrophage migration inhibitory factor activities. This discovery ultimately led to a new course of research, wherein human lymphotoxin preparations were investigated to assess whether human lymphotoxin preparations contained human lymphokines having unique anti-carcinogenic and antitumor properties.

SUMMARY OF THE INVENTION

An object of this invention was to biochemically and biologically characterize and purify the human lymphokine we have discovered which has the anti-tumor properties of directly lysing tumor cells, suppressing their proliferation, and enhancing their susceptibility to natural killer lymphocyte mediated lysis, as well as inhibiting the carcinogenic transformation of normal cells. This object was achieved by identifying and isolating leukoregulin, a lymphokine of about 12,000 to 140,000 molecular weight, with subunits on dissociation of about 30,000 to 35,000 molecular weight, that is purified by isoelectric focusing at pH's of between about 4.8 and 5.5 or between about 7.5 and 8.3.

Another object was to identify the cellular sources of leukoregulin and develop procedures for stimulating its production. We found that peripheral blood leukocytes, a source of leukoregulin, could be stimulated to enhance the production of leukoregulin by exposure for an effective period of time to phytohemagglutinin. The optimum period of exposure was 48 hours, longer and shorter periods were still effective, although to a lesser degree. Other inducers were also found to enhance leukoregulin production, for example, tetradecanoyl phorbol acetate, concanavalin A, and other plant lectins that are mitogenic. In addition, effective leukoregulin producing cells were prepared in some cases by the transformation of lymphocytes and the formation of hybridoma cells.

A further object of the invention was to provide a rapid assay for cell susceptibility to leukoregulin, which was accomplished by preparing hybridomas or transformed leukocytes producing monoclonal antibodies specific for leukoregulin cell surface receptors and quantitating the binding of the antibodies to the target cell being examined.

Additional objects and attributes of the invention will be revealed in the discussion which follows.

BRIEF DESCRIPTION OF THE DRAWINGS

The accompanying FIGS. 1 through 11 illustrate the characteristics and activities of leukoregulin as distinguished from other lymphokines.

DESCRIPTION OF THE PREFERRED EMBODIMENTS

We have discovered that human lymphokine preparations contain a unique lymphokine with the ability to inhibit the growth of human tumor cells by direct lysis, inhibit cellular proliferation, and enhance the susceptibility of tumor cells to natural killer cell (NK) mediated destruction. We have adopted the term leukoregulin for this lymphokine because it is a leukocyte product and a cell growth regulatory substance that is molecularly and biologically distinct from lymphotoxin, interferon, interleukins 1 and 2, and macrophage activating factor activities.

Leukoregulin has a molecular weight of about 120,000 to 140,000, as determined by gradient polyacrylamide gel electrophoresis and gel filtration chromatography, with subunits on dissociation of about 30,000 to 35,000 molecular weight. It purifies by isoelectric focusing at pH's of approximately 5.0 and 7.5. Leukoregulin fractionated according to molecular weight and isoelectric focusing is obtained free of detectable lymphotoxin, interferon, interleukins 1 and 2, and macrophage activating factor activities.

A particular effort was made to ascertain that the characteristics we attribute to leukoregulin are distinguishable from those of lymphotoxin. The lines of evidence demonstrating that leukoregulin is distinct from lymphotoxin are as follows: (1) lymphotoxin from human peripheral blood leukocytes and highly purified lymphotoxin from RPMI 1788 human lymphoblastoid cells, while readily lysing murine alpha L929 tumor cells, does not possess any detectable antihuman tumor cell activities; (2) leukoregulin activity decreased after protease but not neuraminidase digestion, while lymphotoxin activity was decreased after both protease and neuraminidase treatment; and (3) leukoregulin could be separated from lymphotoxin by isoelectic focusing into species which caused the lysis, growth inhibition and enhancement of human tumor cells to cytolysis by natural killer cells but which did not lyse murine L cells (the activity of lymphotoxin). Thus the combination of divergent leukoregulin/lymphotoxin concentrations in PBL lymphokine preparations, sensitivity to neuraminidase and proteases, and differing isoelectric points conclusively demonstrated that leukoregulin is distinct from lymphotoxin.

Leukoregulin is also distinct from interferon, another immunologic hormone able to inhibit cellular proliferation. Interferon has been shown to inhibit the growth of some normal and tumor cells (2,18). However, alpha and gamma interferon did not affect the proliferation of any of the leukoregulin sensitive tumor cells described herein. Although some human lymphokine preparations contain both leukoregulin and interferon, the two hormones can be separated by molecular sieving. Interferon enriched fractions, moreover, do not display leukoregulin activity.

In addition to the inhibition of tumor cell proliferation, purified fractions enriched in leukoregulin have also been shown to enhance the susceptibility of tumor cells to NK-mediated cytotoxicity. This activity is opposite to that of interferon (33), and is unique for leukoregulin. The enhancement of NK-mediated cytotoxicity is thought to be an important means whereby leukoregulin controls the growth of tumors in vivo (27).

An important aspect of the mechanism of leukoregulin activity is its ability to alter the cell surface membrane conformation and the permeability of tumor cells. Flow cytometric analysis was used to measure these changes within minutes following target cell exposure to leukoregulin. This method offers great potential for investigations requiring short assay periods such as detecting monoclonal antibodies to leukoregulin or to the leukoregulin receptor.

The relationship between leukoregulin and tumornecrosis factor, another tumor cell inhibitory lymphokine, was also investigated. Human tumor necrosis factor preparations include hemorrhagic necrosis of some mouse sarcomas in vivo and have the same in vitro activity as lymphotoxin (34). As purified leukoregulin does not mediate the same biological activity as lymphotoxin, leukoregulin is distinct from tumor necrosis factor.

Hamster lymphokine preparations contain lymphotoxin, a leukoregulin activity (growth inhibition of hamster tumor cells but not normal hamster cells) and an anticarcinogenic activity. The leukoregulin activity and the anticarcinogenic activity copurify; however, these two activities have two isoelectric pH's, one which is distinct from hamster lymphotoxin and one which is identical to hamster lymphotoxin (24). Hamster lymphotoxin is degraded by neuraminidase while the leukoregulin and anticarcinogenic activities are unaffected. Hamster leukoregulin and anticarcinogenic activities are, however, similarly susceptible to protease digestion. From this, in conjunction with the other biochemical data, we conclude that hamster leukoregulin also possesses anticarcinogenic activity. As human leukoregulin has demonstrated the same biological and biochemical characteristics as hamster leukoregulin, it should also be anticarcinogenic.

When regulatory approval for clinical trials for the experimental use of leukoregulin in the treatment of human cancer is obtained, Phase I clinical trials with patients having advanced stage neoplastic diseases will be conducted. The patients will be given leukoregulin as described below. Dosages will be increased to establish the maximum tolerable dose for each form of therapy by evaluating toxic reactions manifested by gastrointestinal distress, anemia, leukopenia, fever or other evidence of organ damage and dysfunction. It is expected that leukoregulin will be very well tolerated, permitting administration of high doses. Treatment efforts using partially purified PHA stimulated peripheral blood lymphocyte supernatants that undoubtedly contained leukoregulin have indicated very little toxicity with such materials (13).

Phase II clinical trials will focus on evaluation of leukoregulin in patients with limited diseases, with whom therapeutic benefits will be most apparent. Initial trials will use leukoregulin as an adjuvant to primary surgical, chemo- or radiotherapy, later trials may evaluate leukoregulin as a primary treatment modality.

Leukoregulin will be administered systemically by the intravenous or intralymphatic route, locally by intratumoral injection or peritoneal lavage, or as ex-vivo therapy. An example of the last is where bone marrow cells are removed from the patient, treated with leukoregulin to remove tumor cells, and used to reconstitute the bone marrow of the patients after their bone marrow has received very high doses of chemo- or radiation therapy.

Leukoregulin will be administered as a continuous infusion or as individual injections, as required to maintain the necessary levels of leukoregulin within the circulatory system and tissues.

As an alternative to direct administration, cloning leukoregulin encoding genes into human lymphoid cells rendered incapable of proliferation would provide an approach to maintaining consistent in vivo leukoregulin concentration through in vivo production. Use of cells with a limited in vivo lifespan would insure that leukoregulin levels would be controllable over relatively short periods.

Other alternatives to direct administration include inserting leukoregulin encoding genes into a viral genome and using the virus to carry the genes into a specific group of cells which translate the genes into leukoregulin, circumventing normal regulatory products that would otherwise limit leukoregulin production. For example, the Epstein-Barr virus, which infects only B lymphocytes and usually produces a limited, rather mild infection, could function as an appropriate viral vector for leukoregulin genes if the viral genome is altered to prevent disease progression due to the virus infection.

Treatment of solid tumors will be most effectively performed by maximizing the leukoregulin concentration in the immediate environment of the tumor, rather than trying to maintain a very high concentration throughout the body. Human monoclonal antibodies with qualitative or quantitative specificity for tumor cell surface antigens will provide an appropriate "hook" to which leukoregulin can be coupled to insure high concentrations within tumors. Another approach is to encapsulate leukoregulin within liposomes, which may have tumor specific monoclonal antibodies on their surfaces. Appropriate selection of liposomal triglycerides provides for liposomes which are resistant to circulating amylase enzyme and are capable of fusing with tumor cell membranes for intracellular transport of their leukoregulin contents. Lipophilic carrier substances (Dimethyl sulfoxide, boronic acid derivatives) may be included within the liposome to increase transport of its contents through enhanced fusion of its membrane lipid with those of the tumor target cell.

Leukoregulin appears to augment the anti-tumor activities of chemotherapeutic agents (19) without adding to their toxic side-effects, thus producing a much higher effective does level. Leukoregulin will, therefore, be applied in treatment regimes with various chemotherapeutic substances and radiation therapy to evaluate this anti-tumor enhancing activity.

Leukoregulin's anti-carcinogenic activities are as important as its anti-tumor activity when used with cytotoxic chemotherapeutic agents or radiotherapeutic procedures. A particularly insidious sequence associated with radiation exposure and chemotherapy is the occurrence of new neoplasms unrelated to the disease being treated. With the concommitant administration of leukoregulin, much higher dosages may be used in chemotherapy or radiation treatment because leukoregulin will block with carcinogenic effects of these agents. Leukoregulin will be useful in a similar way when used with immunosuppressive drugs in the treatment of patients having autoimmune diseases and transplant recipients.

Leukoregulin is a terminal component of a cytokine-lymphokine cascade that includes the recruitment and immobilization of lymphocytes and monocytes, their activation or differentiation to express various effector functions, and the production of factors, such as leukoregulin, which execute the cytotoxic functions. Various lymphokines used as a cocktail or, more probably, administered in an appropriate sequence should enhance lymphoid cell infiltration of a tumor (macrophage migration inhibitory factor, interleukin-1), stimulate their cytotoxic function (macrophage activating factor, interleukins 1 and 2, leukoregulin, and interferon), directly attack tumor cells (leukoregulin, NK cytotoxic factor, and interferon), and render tumor target cells more susceptible to the cytotoxic effector cells (leukoregulin). In this form of therapy leukoregulin will have a very important role.

In addition to tumor cell growth regulation and NK cell mediated cytotoxicity enhancement activities, which together stop the growth of and begin to reduce tumor masses, leukoregulin also exhibits anticarcinogenic characteristics that will be especially useful for use in conjunction with materials used in biomedical diagnostic evaluations and in radiation or chemotherapy, which themselves can induce carcinogenesis (26). Treatment with leukoregulin during procedures which have these possible side effects will prevent carcinogenesis during the term of the tests or therapy (20).

In the same manner, patients can be evaluated for their level of immunosuppression and potential risk for forming malignancies by measuring their PBL leukoregulin production after stimulation.

As an adjunct to leukoregulin therapy, determination of the susceptibility of a patient's cancerous cells to leukoregulin would be predictive of the efficacy of leukoregulin treatment. Culturing a patient's tumor cells in the presence of leukoregulin containing, semi-solid medium is a means of quantitating the amount of leukoregulin which is necessary to completely inhibit the growth of the tumor cells. A more rapid assay is one in which the responsiveness of the tumor cells is determined by quantitating the amount of leukoregulin cell surface receptor that is expressed on the tumor cell. This is done by measuring the amount of monoclonal antibody directed to the leukoregulin receptor that binds to the tumor cells using an enzyme linked immunosorbant assay, radioimmuno assay or immunofluorescent assay.

EXAMPLE 1

The abbreviations used in the course of the following discussion are: PBS, 0.14M NaCl, 0.1M sodium phosphate, pH 7.4; PEG, polyethyleneglycol, molecular weight 4000; FBS, fetal bovine serum; IEF, isoelectric focusing; HPLC, high performance liquid chromatography; NK, natural killer lymphocyte; dThd, thymidine; MTT, 3-(4,5-dimethylthiazolyl-2)-2,5-diphenyltetrazolium bromide; FDA, fluorescein diacetate; VCN, Vibrio cholera neuraminidase; PHA, phytohemagglutinin; PBL, peripheral blood leukocyte; TPA, tetradecanoyl phorbol acetate; ELISA, enzyme linked immunosorbant assay; RIA, radioimmunoassay.

LYMPHOKINE PREPARATION

Ten-to-twenty ml of buffy coat leukocytes of centrifuged human normal donor blood were layered on 10 ml of lymphocyte separation medium (LSM, Litton Bionetics, Kensington, Md.) and centrifuged at 700×g for 20 minutes at room temperature. Mononuclear cells were collected at the interface of the LSM and plasma, washed twice with RPMI 1640 medium, and enumerated microscopically in the presence of 0.04% trypan blue to determine viability, which always exceeded 95%. Twenty million cells were plated in 20 ml RPMI 1640 with 10 μg PHA/ml (PHA type IV leukoagglutinin, Sigma Chemical Co., St. Louis, Mo.) in a 100 mm plastic tissue culture dish and incubated at 37° C. in 5% $CO_2$, 95% air, humidified incubator.

After 24, 48 or 72 hours, the lymphocyte culture medium containing the secreted lymphokines was collected and centrifuged for 10 minutes at 1000 x g to remove cells. The lymphokine medium was concentrated 40-fold over a YM10 membrane in an Amicon cell (Amicon, Inc., Danvers, MA) and diafiltered against PBS-0.1% PEG. The concentrated lymphokine was filter sterilized, aliquoted, frozen at −30°, and used within 1 month after freezing. (See Table 1.)

Highly purified human lymphotoxin produced by the lymphoblastoid cell line RPMI 1788 (1) was generously provided by Dr. Bharat B. Aggarwal (Genentech, Inc., San Francisco, CA). The 1788 cell line lymphotoxin was purified through sequential DEAE cellulose chromatography, preparative isoelectric focusing, lentil lectin Sepharose chromatography and preparative and polyacrylamide gel electrophoresis (1). The purified lymphotoxin had a molecular weight of 20,000, an isoelectric point of 5.8, and a specific activity of $4 \times 10^7$ units/mg protein.

Syrian golden hamster lymphokine was produced from peritoneal leukocytes in a manner similar to human lymphokine as previously described (24).

TARGET CELLS

K562 human erythroleukemia cells were provided by Dr. Julie Djeu (Bureau of Biologics, Food and Drug Administration, Bethesda, MD). OST cells established in culture in our laboratory were derived from a freshly excised human osteosarcoma, kindly provided by Dr. Elizabeth Grimm (NIH Clinical Center, Bethesda, MD). Normal human skin fibroblasts, CRL 1457 (20 yr. female), CRL 1505 (21 yr. male), CRL 1537 (14 yr. male), normal colonic mucosal cells, and all other human tumor cell lines were obtained from the American Type Culture Collection (Rockville, MD).

All cells were maintained and subpassed once a week in Eagles minimal essential medium (MEM) supplemented with 10% FBS with the exception of the K562 cells which were maintained in RPMI 1640—10% FBS. Murine alpha L929 cells were a gift from Dr. Gale Granger (USC, Irvine, CA) and are used as a target for lymphotoxin (7). 7997 cells are a benzo(a)-pyrene-induced tumor cell line of Syrian golden hamsters (8).

LYMPHOTOXIN ASSAY

Lymphotoxin activity was measured as the lysis of murine alpha L929 cells using a radionuclide release assay (7). The number of cytolytic lymphotoxin units in a preparation was determined by plotting the regression line of the log of the reciprocal of the sample dilution which caused a 50% release of the [$^3$H]-dThd label in $1 \times 10^4$ alpha L929 cells during 3 days incubation. (See Table 2.)

LEUKOREGULIN ASSAY

Human leukoregulin activity was measured as the growth inhibition (cytostatic activity) of human tumor cells. For the cytostatic activity, $10^4$ tumor cells in 0.5 ml of appropriate culture medium were plated in 24-well culture plates (Costar, Inc, Cambridge, MA). Either medium or test samples diluted over a hundred-fold range in 0.5 ml were added in triplicate and the cells incubated at 37° C. in a 5% $CO_2$:95% air, humidified chamber for 3 days. Nonadherent cells were quantitated by suspending in 9 ml of Hematal and counting with a model ZBI Coulter Counter (Coulter Instruments, Inc., Hialeah, FL). Adherent cells were detached by incubation at 37° C. for 1 min in 0.02% trypsin in PBS before counting as with adherent cells. (See Table 2.)

In some experiments inhibition of cell growth was determined using a micro assay. In this assay, $2 \times 10^3$ cells in 100 µl of RPMI 1640 −10% FBS were plated into 96-well microtiter plates. Then 100 µl of medium, 0.5% SDS, or lymphokine sample were added in quadruplicate and the plates incubated at 37° C. in a humidified 95% air:5% $CO_2$ chamber for 3 days. Flat-bottom plates were used for adherent cells and round bottom for K562 nonadherent cells. Twenty µl of MTT (Sigma) (5 mg/ml PBS—dissolved with vigorous agitation and freshly prepared before use) were added to each well. The plates were incubated an additional 4 hours at 37° C. and the media removed by gentle aspiration with an 18 g needle. The reduced MTT, a purple formazan precipitate, was solubilized by adding 100 µl 0.05M HCl in isopropanol. The absorbance of the dye was read at 540 nm with an ARTEK automated vertical beam reader (ARTEK Systems, Inc., Farmingdale, N.Y.). The sample well containing the SDS was used as a blank and was substrated from all other sample readings. In preliminary experiments, cells were seeded at varying densities, and the amount of reduced precipitate formed was found to be directly proportional to the number of cells per well. The microassay was comparable in sensitivity to the cell count assay.

The percent inhibition of cell growth in either assay was calculated as the ratio of the mean number of cells or absorbance units of test sample divided by the number of cells or absorbance units in medium control wells, minus 1, times 100%. Leukoregulin cytostatic units were determined by plotting the regression line of the log of the reciprocal of the sample dilution vs. the % growth inhibition, and equaled the reciprocal of the dilution which caused a 50% inhibition of cell growth. The human colon carcinoma cell line HT-29 is highly susceptible to the growth inhibitory activity of leukoregulin and was used as the standard for measuring leukoregulin, against which other cells were compared.

For the cytolytic activity, tumor cells were prelabeled with [$^3$H-]dThd (7) and plated at $10^4$ cells in 0.5 ml/well in 24-well plates. One half ml of medium, 0.5% sodium dodecyl sulfate (SDS), or test sample diluted over a hundred-fold range were added in triplicate and the cells incubated for 3 days.

The plates were centrifuged at $200 \times g$ for 10 min. and 200 µl aliquots of the supernatants were removed, suspended in 2.8 ml of Ultrafluor (NEW, Boston, MA), and counted in a LKB Scintillation counter (LKB Instruments, Inc., Rockville, MD). The percent specific [$^3$H]-dThd released was calculated as follows: % specific [$^3$H] release—Mean CPM sample—Mean CPM Medium Mean $CPM_{SDS}$—Mean $CPM_{medium}$ The number of cytolytic leukoregulin units were calculated in the same manner as lymphotoxin cytolytic units.

CARGINOGENESIS ASSAY

The inhibition by Syrian golden hamster lymphokine preparations of the chemical and radiation-induced transformation of Syrian golden hamster fetal cells was studied using an in vivo—in vitro transplacental transformation assay, as previously described (24,25). (See Table 3.)

INTERFERON ASSAY

Interferon was assayed by Biofluids, Inc. (Rockville, MD) by determining the inhibition of the semi-microcytopathic effect caused by bovine vesicular stomatitis infection of human neonatal foreskin fibroblasts or WISH cells. The human WISH cell line is 5- to 10-fold more sensitive to gamma interferon than are human foreskin cells. The limit of detection in this assay is 1 unit of antiviral activity which is standardized against NIH reference human fibroblast interferon. (See Table 4.)

In some experiments the effects of alpha and gamma interferon on cellular bioassays were determined. Alphainterferon (purchased from Sigma) was produced in Burkitt lymphoma cells (Namalva) by induction with Sendai virus and had a specific activity of $1.1 \times 10^6$ International Reference units/mg protein. Gamma interferon with a specific activity of $10^5$ antiviral units/ml was kindly provided by Dr. Gary Thurman (NCI, Frederick Cancer Research Facility, Frederick MD) and was prepared by Flow Laboratories, Inc. (McLean, VA) and Meloy Laboratories (Springfield, VA) for the Biological Response Modifiers Program (NCI Frederick Cancer Research Facility, Frederick, MD). (See Table 5.)

INTERLEUKINS 1 and 2

Interleukin 1 activity was determined by measuring the enhancement by lymphokine of the proliferation of C3H/HeJ murine thymocytes responding to PHA (18).

Thymocyte proliferation may also reflect the presence of interleukin 2; therefore, lymphokine was also tested for interleukin 2 using a standard microassay (3,22) based on the interleukin 2 dependent proliferation of the OH-1 marmoset continuous T cell line sensitive to human interleukin 2. A human interleukin 2 standard (provided by Dr. P. Jagannath, Litton Bionetics, Inc., Kensington, MD) had a half maximal proliferation enhancement at a dilution of 1:1500. A human interleukin 1 standard was prepared in our laboratory using the lymphokine production method described herein. (See Table 4.)

MACROPHAGE ACTIVATION AND ENDOTOXIN ASSAYS

These two assays were kindly performed by Dr. Gary Thurman, NCI, Frederick Cancer Research Facility, Frederick, MD. Macrophage activation activity was measured as the ability of lymphokine to enhance the cytotoxic activity of human monocytes for human tumor cells (14). Endotoxin was determined by a chromogenic assay (Endotoxin chromogenic assay kit, M.A. Bioproducts, Walkersville, MD), sensitive to approximately 0.1 ng. The possible contribution of endotoxin to tumor cell growth inhibition was also examined. Endotoxin (lipopolysaccharide) with serotype numbers 055:B5 and 0111:B4 (Sigma) was added to the tumor cell cytostatic assay at concentrations of 0.01, 0.1, 1.0, 10.0 and 20 ng/ml. The effect on tumor cell growth was measured as above. (See Table 4.)

ISOELECTRIC FOCUSING

Preparative column isoelectric focusing of the concentrated lymphokine samples was performed within a pH 3.5–10 ampholine (LKB, Rockville, MD) gradient in a 110 ml isoelectric focusing column (LKB) (28). Three ml fractions were collected and the pH of each fraction measured. Selected fractions were pooled, diafiltered against PBS—0.1% PEG, filter sterilized with a 0.22 μ Millex filter (Millipore Corp., Bedford, MA) and assayed for biological activity. (See Table 4 and FIG. 8.)

HPLC

Separations based on molecular size were performed using a preparative Toyasoda G3000 SWG gel HPLC column (distributed by LKB). Two ml samples were isocratically eluted at a flow rate of 4 ml/min with 0.02M sodium phosphate buffer, pH 7.4 with 0.1% PEG. Four ml fractions were collected, filter sterilized, and assayed for biological activity. (See FIG. 4.)

HPLC separation based on molecular charge was performed in a Toyasoda DEAE-545 analytical anion exchange column. Samples in 20 mM Tris HCl, pH 7.4 with 0.1% PEG were eluted with a linear 1 hr. gradient of 0.5 m NaCl at a flow rate of 0.75 ml/min. Two minute fractions were collected, filter sterilized and assayed. (See FIG. 9.)

POLYACRYLAMIDE GEL ELECTROPHORESIS

Concentrated leukoregulin samples (either unfractionated or separated by HPLC gel filtration and ion exchange chromatography) were electrophoresed on 4–30% linear gradient polyacrylamide gels (16). After electrophoresis, the gels were sliced into 0.25 mm segments and the slices eluted overnight in medium—10% FBS. Eluates were filter sterilized and assayed. (See FIG. 5.)

Purified leukoregulin labelled with $^{125}I$ was also electrophoresed on 15% polyacrylamide gels with a 5% acrylamide stacking gel containing 1% sodium dodecyl sulfate (15). The sample was visualized by autoradiography. (See FIG. 7.)

RADIOLABELLING OF PURIFIED LEUKOREGULIN

Twenty five units of leukoregulin purified by sequential HPLC and polyacrylamide gel electrophoresis were labelled with $^{125}I$ using the chloramine T method (17) and adding bovine serum albumin as a carrier protein to separate the labelled leukoregulin from unreacted $^{125}I$ on a Sephadex G-10 column.

GEL FILTRATION COLUMN CHROMATOGRAPHY $^{125}I$-labelled purified leukoregulin was eluted on a S-300 (Pharmacia Fine Chemicals, Upsala, Sweden) column with 10 mM NaPO$_4$ buffer—1.0M NaCl, pH 7.4. Two ml fractions were collected and counted. (See FIG. 6.)

ENZYMATIC DIGESTION

The susceptibility of human and hamster leukoregulin and lymphotoxin activities to neuraminidase and protease digestion was evaluated (29). One-half ml of a concentrated human or hamster lymphokine preparation was added to 50 μl of VCN (500 units/ml, Calbiochem-Behring Corp., LaJolla, CA) and 0.5 ml of 0.1M sodium acetate buffer pH 5.1. As controls, 0.5 ml of lymphokine was added to 0.5 ml of the acetate buffer, 0.5 ml of the acetate buffer containing 50 μl of VCN and 50 μl of 0.2M sialic acid (Sigma) (this concentration of sialic acid inactivates the enzyme, or 0.5 ml of medium. Samples were incubated for 60 minutes at 37° C., dialyzed against PBS-PEG in an Amicon cell with a YM10 membrane, and sample volumes adjusted to 3 ml. For proteolytic digestions, 1 ml of lymphokine samples was added to 1 ml of trypsin in PBS (32 units/ml, specific activity 195 units/mg, Worthington Enzymes Inc., Freehold, NJ), 1 ml of chymotrypsin in PBS (6 units/ml, specific activity 59 units/mg, Sigma), or 1 ml of pronase (6 units/ml, specific activity 6 units/mg, Sigma) in 0.1M Tris base with 3 mM CaCl$_2$ and 3% toluene. Pronase was activated by incubating 10 mg pronase/ml 0.1M Tris—15 mM CaCl$_2$, pH 7.8 for 30 minutes at 37° C. just before adding to the sample. Samples were proteases or protease buffer controls were incubated at 60 min at 37° C. One ml of FBS was added to each sample and samples were diluted over a hundred-fold range in medium for assay. (See Table 3.)

NK CYTOTOXICITY ASSAY

Enhancement of target cell susceptibility after leukoregulin treatment to NK-mediated cytotoxicity was determined essentially as previously described (23). Normal human peripheral blood mononuclear cells isolated by LSM gradient centrifugation were passaged through nylon wool to remove macrophages and B cells while enriching for NK cells. K562 target cells were labeled 18 hours by addition of 100 $\mu$ Ci $^{51}$Cr as sodium chromate (NEN, Boston, MA). Target cells were washed 3 times with 1640—10% FBS and suspended to $2.5 \times 10^5$ cells/ml of medium or lymphokine sample diluted in medium. The target cells were the incubated 30 min at 37° C., centrifuged at 280 xg for 5 min and resuspended in 1640—10% FBS at a concentration of $10^5$ cells/ml. One hundred $\mu$l of cells were added to tubes containing 100 $\mu$l of medium or effector cells at 25:1, 10:1, or 2.5:1 effector to target cell ratios. A 4-hour $^{51}$Cr-release assay was then performed (23). Spontaneous $^{51}$Cr release ranged from 15 to 20% whether the cells were preincubated in medium or lymphokine. The degree of lympholine enhancement was determined by comparing lytic units of NK cytotoxicity of target cells incubated in medium to target cells incubated in lymphokine. One lytic unit, defined as the number of lymphoctyes causing a specific release of 15% of $^{51}$Cr from the target cells, was calculated using the Van Krough equation (21,32). (See Table 6 and FIG. 3.)

FLOW CYTOMETRIC ANALYSIS

K562 cells were resuspended at $4 \times 10^6$/ml in RPMI 1640—10% FBS. Into $12 \times 75$ mm plastic tubes, 250 $\mu$l of cell suspension was dispensed with the addition of 250 $\mu$l of lymphokine sample. The tubes were incubated at 37° C. in a 5% $CO_2$:95% humidified air atmosphere on a platform rocket (Bellco Glass Co., Vineland, NJ) at 6 cycles/minute for 30 minutes to 6 hours.

Instrumentation: Flow cytometric analyses were performed using a FACS IV fluorescence activated cell sorter (Becton-Dickinson, Sunnyvale, CA) equipped with a 5W argon-ion laser as the excitation source, a 256 channel pulse height analyzer, and logarithmic amplifiers. The cells were analyzed for narrow angle forward light scatter and fluorescence after passage through a 70 $\mu$ diameter nozzle in a sheath fluid of MILLI-Q filtered (Millipore Corp., Bedford, MA) $H_2O$. Narrow angle forward light scatter signals, an indicator of cell size and shape, were used as the trigger signal for all analyses. All optical filters were supplied by Becton-Dickinson with the instrument unless specified otherwise.

FDA Fluorochromasia: FDA was used to measure cell membrane permeability (5). A stock solution of FDA (Polyscience, Inc., Warrington, PA) was made by dissolving crystalline FDA in acetone to a concentration of 5 mg FDA/ml. Immediately before use, a working solution was prepared by diluting the stock solution in RPMI 1640—10% FBS to give a final concentration of 6.25 $\mu$g FDA/ml. After lymphokine treatment of K562 cells, the cells were washed once in RPMI 1640—10% FBS and resuspended in 1 ml of the working FDA solution at 6.25 $\mu$g/ml, incubated at room temperature for 5 minutes, then analyzed on the flow cytometer.

Propidium iodide fluorochromasia: Propidium iodide was also used to measure cell membrane permeability. A stock solution of propidium iodide (Calbiochem-Behring Corp., La Jolla, CA) was made by dissolving propidium iodide in PBS, pH 7.4, at a concentration of 500 $\mu$g/ml. Immediately before use, a working solution was prepared by diluting the stock solution in PBS to give a final concentration of 0.2 $\mu$g propidium iodide/ml. After lymphokine treatment, the cells were washed once in RPMI 1640—10% FBS and resuspended in 1 ml of the working solution of propidium iodide, incubated for 5 minutes at room temperature, then analyzed on the flow cytometer.

Fluorescence measurements: The excitation wavelength used for both FDA and propidium iodide was the same, 488 nm at 400 mW. Long pass 515 and 520 nm optical glass filters were placed in front of the fluorescence detector photomultiplier tube. When analyzing propidium iodide labeled samples, an additional red additive dichroic filter (Corion Corp., Hollister, MA) was placed in front of the photomultiplier tube. Medium treated K562 cells were used to fine tune the flow cytometer prior to each experiment. The gain controls and the photomultiplier tube voltage were adjusted so 90% of $2 \times 10^4$ cells analyzed would fall within a predetermined range of channels within an entire scale of 256 channels. This was done for each of the 3 parameters (narrow forward angle light scatter, fluorescein fluorescence and propidium iodide fluorescence) investigated in this study. For medium treated control cells scatter and fluorescein fluorescence were set in the upper portion of the channel range and propidium iodide fluorescence in the lower portion so as to measure the appropriate shifts in lymphokine-treated cells. For each K562 cell sample treatment, $2 \times 10^4$ cells were analyzed and the percentage of cells within the predetermined marker region was calculated. This percentage was then substracted from the medium treated control percentage (approximately 90%) resulting in the percent change for the sample. Percent changes ranged from approximately $-5$ to $+70$. A change in the positive direction indicates an effect on the K562 cell caused by the lymphokine treatment for the parameter being measured. (See FIG. 10.)

EXAMPLE 2

PRODUCTION OF HUMAN B CELL LINES AND HYBRIDOMAS SECRETING LEUKOREGULIN

Cancer patients were immunized intradermally with their own dissociated tumor cells that had been irradiated with 20,000 rads and were mixed with $10^7$ viable BCG. Peripheral blood lymphocytes prepared from the venous blood of these patients were mixed with murine NS-1 myeloma cells, at a ratio of 3 PBL per 1 myeloma, centrifuged and resuspended in 100 $\mu$l serum free medium. One ml of polyethylene glycol (50% w/v) pre-warmed to 37° C. was added dropwise to the cell pellet over the course of one minute with constant agitation of the tube. Twice the previous volume of pre-warmed serum-free medium was added to the cell suspension over the course of one minute until the 50 ml tube was filled. The cells were pelleted at 800 RPM for 15 minutes. The cells were gently resuspended in HT medium (DMEM containing 20% fetal bovine serum, hypoxanthine 13.6 $\mu$g/ml and thymidine 3.9 $\mu$g/ml) at a concentration of $2.5 \times 10^6$ cells/ml (pre-fusion count) and 100 μl was added to each microtiter well. Twenty-four hours later, 100 μl of HAT medium (HT medium containing 0.18 μg/ml aminopterin) was added to each well. Half of the medium was replaced every three days with fresh HAT medium. After maintenance in HAT medium for 14 days, the cells were maintained on HT medium for an additional two weeks, at which time the cells were grown on a MEM medium containing 20% fetal bovine serum.

Alternatively, co-cultivation of PBL with myeloma cells may be used to generate transformed diploid B-cells. PBL and myeloma cells were mixed (at a ratio of 3:1), pelleted at 800 RPM and selected in HAT medium, as described above.

Supernatants from the hybridomas or transformed diploid B cells were tested for secreted leukoregulin using the microassay with HT-29 cells as targets. Cells producing leukoregulin were expanded in MEM-10% FBS, and when sufficient numbers were obtained, experiments were performed to determine the optimum conditions for leukoregulin production in serum free medium. Cells were suspended at a concentration of $2 \times 10^5$/ml RPMI 1640 and incubated for 3 days at 37° C. In some experiments, 10 ng tetradecanoyl phorbol acetate/ml was added to the cultures to stimulate leukoregulin production. The supernatants were collected, centrifuged at 800 x g and assayed for leukoregulin activity.

All lines consisting of transformed B cells and hybridomas that produce leukoregulin were deposited on Jan. 30th, 1984 with the American Type Culture Collection (ATCC), 12301 Parklawn Drive, Rockville, Md. 20852, USA. Specific examples are the transformed human B cell line LiCo 16-88, and the human mouse heterohybridoma cell line LiCo 6a3-1. (See Table 1.)

EXAMPLE 3

PREPARATION OF MONOCLONAL ANTIBODIES TO THE LEUKOREGULIN CELL SURFACE RECEPTOR

Balb/c mice were immunized by 3 subcutaneous injections of K562 membranes spaced two weeks apart. Each mouse received membranes equivalent to $10^7$ cells prepared by homogenization with a motor driven Teflon homogenizer, clarified by low speed centrifugation and then collected by ultracentrifugation at 100,000 x g for 1 hr. Membranes were mixed with complete Freund's adjuvant for each of the boosts. Three days prior to hybridization, the mice were injected intraperitoneally with the K562 cell membranes in PBS. On the day of the fusion, the spleens were removed and single cells were obtained and fused at a ratio of 3 spleen cells to 1 myeloma cell with PEG. After fusion, hybrids were selected by culturing in hypoxanthine, aminopterin, and thymidine containing medium (10). Colonies producing antibodies to the leukoregulin receptor were cloned by a limiting dilution method. A hybridoma cell line, designated LrR MP-82-2, prepared as described above, was deposited with the ATCC on Apr. 10th, 1984.

A biological assay measuring the inhibition of leukoregulin directed growth retardation of HT-29 cells was used to detect antibodies to the leukoregulin receptor. Two thousand HT-29 cells were plated in 0.1 ml MEM-10% FBS in wells of a 96-well plate. Sufficient leukoregulin in 0.1 ml to cause a 50% inhibition of HT-29 cell growth was added, followed by 25 μl of the test antibody containing supernatant. After 3 days' incubation, inhibition was measured by quantitation of cells present by staining with MTT as described earlier. Any sample displaying a 25% or greater inhibition of the leukoregulin activity was considered positive. The rationale behind this assay is that the monoclonal antibody will bind to the leukoregulin receptor which thereby inhibits leukoregulin binding and its subsequent growth inhibitory activity.

Quantitation of leukoregulin receptor expression was measured three ways, all of which quantitated the percentage of monoclonal antibody directed to the leukoregulin receptor. In the immunofluorescent assay, $2 \times 10^5$ cells were incubated with the monoclonal antibody for 1 hr. at 37° C. The cells were washed 2 times, a fluorescent conjugated goat anti-mouse immunoglobulin (Kirkegard and Peiry Labs, Rockville, MD) was added and incubated for 30 min. at 4° C. The cells were washed, resuspended in 0.5 ml of PBS and analyzed on a EPICS 5 flow cytometer (Coulter Instruments, Hialeah, FL) using the 488 laser line to excite the green fluorescence. ELISA and RIA were performed in a similar manner except that the conjugate used in ELISA was a horseradish peroxidase goat anti-mouse immunoglobulin and that used in the RIA was $^{125}$I-labelled goat anti-mouse immunoglobulin. The ELISA assay was quantitated colorimetrically by measuring the amount of substrate hydrolized on an ARTEK automated reader. The RIA was quantitated by measuring $^{125}$I-label bound using a LKB gamma counter (LBK) Instruments, Rockville, MD). (See Table 8.)

Example 4

MEASUREMENT OF PATIENT TUMOR CELL SUSCEPTIBILITY TO LEUKOREGULIN USING AN AGAR CLONOGENIC ASSAY

Tumor cells have the unique ability over normal cells to grow in semi-solid medium. This characteristic of tumor cells provides a means for quantitating the effect of cancer therapeutic agents on freshly dissociated cells of excised human tumors. Colon tumors obtained at surgery were minced and dissociated with collagenase and DNAase to obtain single cell suspension (11). The cells were suspended in 0.15% agar in medium according to the procedure of Kern (12), except that leukoregulin was added at varying concentrations. The development of tumor cell colonies growing suspended in the agar medium was quantitated after 10–14 days' incubation. (See Table 9.)

EXAMPLE 5

CLONING OF THE LEUKOREGULIN GENE

Having defined leukoregulin both biologically and biochemically, and having provided, therefore, methods for identifying and isolating leukoregulin, as set forth above, the cloning and expression of leukoregulin is conducted using conventional, widely published approaches and protocols (e.g., Maniatis et al, *Molecular Cloning: A Laboratory Manual*, Cold Spring Harbor Press, Cold Spring Harbor, NY, 1982). These procedures rely on the sensitive bio-assay disclosed in the preceding examples. Having developed the assay and having biologically and biochemically defined leukoregulin, standard recombinant DNA and cloning techniques can be used to produce a protein identical in amino acid sequence and biological activity to authentic natural leukoregulin, or a biologically active subunit thereof, in *E. coli* or in other suitable host organisms. An outline of the cloning procedure is presented in FIG. 11. This procedure is equivalent to the methods conducted with many biological relevant eukaryotic genes, particularly the human lymphokine, lyphotoxin, which was expressed in bacteria using a similar protocol as reported by Gray, P. W., et al, Nature 312, 721 (1984). This article and the other articles cited in this example are to be included herein in their entirety by reference.

The cloning example can be discussed as six distinct phases. (See FIG. 11.) The elements of each of these steps are described below.

Phase I

Bio-Assay, Purification, and Biological Characterization

This analysis must be conducted before any cloning experiments can proceed. The details of these studies are the data presented in this application. After developing this data, as set forth above, it is then possible to proceed with genetic engineering.

Phase II

*E. coli* Gene Library

The construction of bacterial clones is based upon characterization of the natural sources for leukoregulin. As the present application discloses a method for the stimulation of production of leukoregulin by human peripheral blood lymphocytes (PBL), these cells must contain the genetic information required for leukoregulin synthesis and are an obvious source of leukoregulin genes. Using stimulated cell populations, mRNA is isolated that contains leukoregulin mRNA. This PBL mRNA is used to construct cDNA libraries in, for example, *E. coli*, or other host organisms.

Phase III

Biochemical Characterization, Amino Acid Sequence

As discussed above, the leukoregulin protein has been characterized biochemically and purified to homogeneity. The next critical step is to define the amino acid sequence of the leukoregulin protein using this natural material. This work, which is necessary to confirm that any gene clones obtained do correspond to authentic leukoregulin, is conducted by conventional biochemical sequencing methods.

Phase IV

Gene Isolation by Immuno-Screening

This approach to gene isolation can be initiated immediately upon completion of Phase II. The critical reagent for this experiment is anti-leukoregulin antibody directed against the natural leukoregulin, which can be prepared after the purification of sufficient natural leukoregulin to immunize animals. The technique, which has been used successfully to screen *E. coli* gene libraries for various genes is taught by Helfman, D. M., et al, PNAS 80, 31–35 (1983), and Young, R. A. and R. W. Davis, PNAS 80, 1194–1198, (1983).

Phase V

Gene Isolation by DNA Probe

This is an alternative, and most widely used, method for gene isolation from a recombinant DNA *E. coli* library. As originally demonstrated by Noyes et al (PNAS 76, 1770–1774 (1979), a synthetic oligodeoxynucleotide probe is used to isolate and characterize a eukaryotic mRNA. The probe is a small section of the DNA sequence for leukoregulin prepared by first determining a partial amino acid sequence for the native protein, and then synthesizing a nucleotide sequence that codes for that partial amino acid sequence. The synthetic nucleotide sequence can, for example, be prepared chemically, as described by Itakura, K., et al, *J.Am.Chem.Soc.* 97, 7326 (1975). As an example, the amino acid sequence Trp-Met-Glu-Glu from gastrin was used to define a dodecanucleotide d(CTCCTCCATCCA) that specifically hybridizes to gastrin mRNA. For leukoregulin, similarly, the synthetic DNA fragment is used as a probe which hybridizes to the natural mRNA taken from cells that produce leukoregulin. Using for example, a tag and conventional methods, the mRNA for leukoregulin is separated from mixtures of RNA. Methods used in these procedures are discussed in Maniatis et al, supra; Goodman et al, U.S. Pat. Nos. 4,283,489 and 4,363,877, and in the references cited therein.

An extension of these results has been to use such probes in the screening of cDNA libraries [Crea, R. and Horn, T. *Nuc Acid Res* 8, 2331–2348 (1980)]. Recently a set of tetradecanucleotides $$d(TC \underline{A} CA \underline{A} TA \underline{C} TCCA)$$
$$\phantom{d(TC\ }G\phantom{\ CA\ }G\phantom{\ TA\ }T$$

predicted by the amino acid sequence Trp-Glu-Tyr-Cys-Asp was used to detect clones of the human tissue-type plasminogen activator gene cDNA *is E. coli* (Pennica, D., et al, Nature 301, 214–220, 1983).

Phase VI

Gene Assembly, Microbial Expression

The final phase of cloning is the routine assembly of an intact copy of the eukaryotic structural gene and the translation of the gene to produce leukoregulin or a biologically active subunit thereof. Procedures to genetically engineer microbial expression of this gene will proceed along various avenues with different hosts. Although the different options for preparing a vector, transforming a host cell and effecting translation and expression are too numerous to list, the procedures are conventional and have been discussed in numerous reviews, such as Maniatis et al, supra, *Gene Amplification and Analysis: Expression of Cloned Genes in Prokaryotic and Eukaryotic Cells*, Papas, T. S., Rosenberg, M., and Chirigkjian, J. G. (eds.), Elsevier Science Publishing Co., Inc., NY, 1983, Berman et al, U.S. Pat. No. 4,503,142, and in the references cited therein.

It is further conceived within the scope of this invention that a modified form of leukoregulin or a biologically active subunit thereof can be synthesized which may have modifications in its molecular structure. Such modified leukoregulin may demonstrate enhanced usefulness, such as increased efficacy, reduced side effects or increased stability; or it may demonstrate the equivalent activity or a less but adequate activity by which leukoregulin is defined. In all cases, however, where the molecular structure and the biological activity are for the greater part the same as the leukoregulin defined herein, it is to be considered its equivalent or a normal modification thereof and, therefore, part of the present application.

Example 6

ANTIBODY NEUTRALIZATION

Leukoregulin activity is not neutralized by antisera to lymphotoxin, tumor necrosis factor, γ-interferon, or cytolysin. This characteristic is reported by Sayres et al, *J. Immunol.*, 137:1-6, 1986, which is included herein by reference.

DESCRIPTION OF THE FIGURES AND TABLES

FIG. 1

Cytolysis of human tumor cells by human PBL lymphokine containing leukoregulin (O--O), and purified 1788 cell line lymphotoxin (●—●) at equivalent lymphotoxin concentrations. The standard deviation of sample means was maximally 2%.

Human lymphokine and lymphotoxin, however, had little or no cytolytic activity towards human leukemia, sarcoma, and carcinoma cells. A maximum of 50% lysis of the RPMI 2650 carcinoma cells was observed with a lymphokine sample containing 1000 units of lymphotoxin/ml.

FIG. 2

Growth inhibition of human tumor cells by human lymphokine containing leukoregulin (O--O), and purified 1788 cell line lymphotoxin (●—●) at equivalent lymphotoxin concentrations. The standard deviation of sample means was maximally 5%. The % growth inhibition was determined using a cell counting assay.

The highly purified 1788 cell line lymphotoxin failed to lyse each of the three types of tumor cells. Despite low lytic activity toward human tumor cells, human lymphokine caused significant growth inhibition of human tumor cells. The purified 1788 cell line lymphotoxin, however, displayed significant growth inhibition only at concentrations of 500 and 1000 lymphotoxin units/ml. The growth inhibition at these concentrations, moveover, could well have been due to the growth retarding influence of the pH 8.4 ammonium carbonate buffer in which the purified lymphotoxin was prepared.

FIG. 3

Enhancement of target cell susceptibility to NK-mediated cytotoxicity by human lymphokine containing leukoregulin but not by purified human lymphotoxin. Human lymphokine with 40 lymphotoxin units/ml (O--O), purified 1788 lymphotoxin at 40 units/ml (●—●), or media (Δ—Δ) were incubated 30 mins with target cells before addition of NK effector cells. The standard deviation of sample means was maximally 1%.

In addition to inhibiting tumor cell proliferation, human lymphokine, but not purified 1788 lymphotoxin, enhanced the susceptibility of human carcinoma, leukemia, and sarcoma cells to NK-mediated cytotoxicity. Human lymphokine even caused lysis of RPMI 2650 carcinoma cells which are resistant to NK lysis. Purified 1788 lymphotoxin failed to enhance the susceptibility of carcinoma, leukemia, or sarcoma cells to lysis by NK. The divergent biological activities of unfractionated human PBL lymphotoxin containing lymphokine and purified 1788 cell line lymphotoxin suggest that a lymphokine other than lymphotoxin mediates the antitumor cell activities.

FIG. 4

Gel permeation HPLC of two different human lymphokine preparations

Two ml samples were diluted isocratically from a Toyasoda TSK G-3000 SWG column with 20 mM Na phosphate buffer pH 7.4 containing 0.1% PEG. Four ml fractions were collected, diluted over a hundred-fold range with RPMI 1640—10% FBS, and assayed for lymphotoxin cytolysis of alpha L929 cells and leukoregulin cytostasis of human K562 and 2650 tumor cells. The protein absorbance profile at 280 nm is shown in the alpha L929 assay panel.

The apparent molecular weight of human PBL lymphotoxin and leukoregulin was examined by HPLC molecular sieve chromatography. The majority of the lymphotoxin activity eluted in fractions within the 30,000–40,000 molecular weight range. There was, however, some variation in samples from different individuals with some also having lymphotoxin activity within the 50,000–70,000 and 12,000–20,000 molecular weight range. Leukoregulin activity eluted in fractions within the 50,000–70,000 molecular weight range with a minor component in the 10,000–15,000 molecular weight range.

FIG. 5

Linear gradient polyacrylamide gel electrophoresis of leukoregulin

A more accurate estimation of the molecular weight of leukoregulin was determined by gradient polyacrylamide gel electrophoresis. One ml of a human leukoregulin preparation was electrophoresed overnight. The gel was then sliced and the slices were eluted overnight with MEM-10% FBS at 37° C. Leukoregulin activity (open circles) was measured using the microassay with HT-29 carcinoma cells as the targets. Leukoregulin migrated with proteins of molecular weights of 110,000–140,000. As shown in this figure is the electrophoretic pattern of $^{125}$I-labelled (closed circles) leukoregulin purified by sequential HPLC gel filtration, ion exchange chromatography, and linear gradient polyacrylamide gel electrophoresis.

FIG. 6

Gel filtration of purified leukoregulin

An alternative method for molecular weight determination using Pharmacia S-300 gel filtration was employed. Leukoregulin purified by HPLC gel filtration, ion exchange chromatography and linear gradient polyacrylamide gel electrophoresis was labelled with $^{125}$I and eluted on a S-300 column with 10 mM NaPO$_4$ buffer, pH 7.4–1.0M NaCl. The purified leukoregulin had an apparent molecular weight of 120,000–140,000 by this procedure.

FIG. 7

Sodium dodecyl sulfate polyacrylamide gel electrophoresis

Purified leukoregulin labelled with $^{125}$I was electrophoresed on a sodium dodecyl sulfate polyacrylamide gel to determine whether the native protein would dissociate into subunits when subjected to denaturing conditions. Leukoregulin electrophoresed with 30,000–35,000 molecular weight molecules, as shown by this autoradiograph of the gel.

FIG. 8

Isoelectric focusing of two different human lymphokine preparations

Two ml samples were focused in a pH 3.5–10 gradient. Three ml fractions were collected, the pH of each fraction determined and consecutive fractions with 0.5 pH units pooled, diafiltered against PBS-PEG, sterile filtered, diluted over a hundred-fold range and assayed for lymphotoxin cytolytic activity on alpha L929 cells (●—●) or leukoregulin cytostatic activity on K562 (□--□) and OST (○--○) cells.

Although human lymphotoxin and leukoregulin activities overlapped when separated by molecular sieving, the two activities could be separated based on differences in molecular charge. Lymphotoxin had an isoelectric pH between 6.5 and 7.2. Leukoregulin had two isoelectric pH's: one between 5.0 and 5.8, the second between 7.5 and 8.3.

FIG. 9

HPLC ion exchange chromatography of leukoregulin and lymphotoxin

Two ml samples of a human lymphokine preparation were separated on a DEAE-545 HPLC column by eluting with a linear 0–0.5M NaCl gradient. Fractions were filter sterilized and assayed for leukoregulin using a microassay and HT-29 target cells or for lymphotoxin. Leukoregulin eluted at a 0.1M NaCl concentration and was separated from lymphotoxin which eluted at 0.15M NaCl concentration.

FIG. 10

Flow cytometric analysis of leukoregulin activity

Another biological activity of leukoregulin which may be related to its mechanism of action was assessed by flow cytometric analysis. Changes in K562 cell volume or membrane permeability detectable by alterations in narrow angle forward light scatter (○) or by fluorescein diacetate (○) or propidium iodide (△) fluorochromasia were assessed using 488 nm argon laser line excitation in a FACS IV flow cytometer. In the top chart, K562 cells were treated with a lymphokine preparation containing 10 (——), 40 (···), or 100 (—•—) units of diafiltered lymphotoxin or 500 (—) units of alpha interferon for 0–6 hours to establish the response of the cells to the lymphokine.

When lymphokine was added to K562 cells, the narrow angle forward light scatter from the cells decreased, propidium iodide fluorochromasia increased, and FDA fluorochromasia descreased. The change in narrow angle forward light scatter reflected a change in cell shape and/or size with an increase in cell volume confirmed by cell volume analysis on a Model ZB1 Coulter Counter with added Accucomp cell volume analysis programming (Coulter Instruments, Inc., Hialeah, FL). The decrease in FDA fluorochromasia reflected increased membrane permeability, as the fluorescent intracellular fluorescein escapes from the cell. The increase in propidium iodide fluorochromasia also reflected an increase in membrane permeability as propidium iodide entered the cell and intercalated with nucleic acid. Flow cytometric changes caused by human lymphokine were detectable 30 min. after treatment of K562 cells and were maximal by two hours. Alpha interferon did not induce any changes during that time period in cell surface conformation or plasma membrane permeability. In the lower chart, K562 cells were treated with the HPLC-isoelectric focusing fractions (sample numbers from Table 4) for 2 hours and the change in light scatter (—), and in fluorescein diacetate (——) and propidium iodide (. . .) fluorochromasia measured. Lymphokine cell conformation and membrane permeability activity were present only in HPLC and isoelectric focusing purified leukoregulin fractions. Fractions enriched in lymphotoxin or in the interleukins and interferon produced no detectable cellular conformational or plasma membrane permeability changes.

FIG. 11

Cloning of the Leukoregulin Gene

This flowchart diagram presents the six distinct phases entailed in cloning the leukoregulin gene. (See Example 5.)

FIG. 12

Cation Exchange Chromatography

Leukoregulin was separated from other proteins by first binding to and then elution from a cation exchange medium. Leukoregulin partially purified by Blue A Agarose, Phenyl Sepharose and DEAE chromatography was dialyzed versus 20 mM $KPO_4$ buffer at pH 6.3 and eluted onto a Poly CAT$^{TM}$ (Poly LC, Columbia, Md.) cation exchange HPLC column. A linear gradient of 0–0.5M NaCL at a flow rate of 1 ml per minute resulted in leukoregulin activity eluting at an 0.1M NaCl in 20 mM $KPO_4$ buffer at pH 6.3 with greater than 80% recovery of activity.

FIG. 13

Reverse Phase Chromatography

Figure 13A:
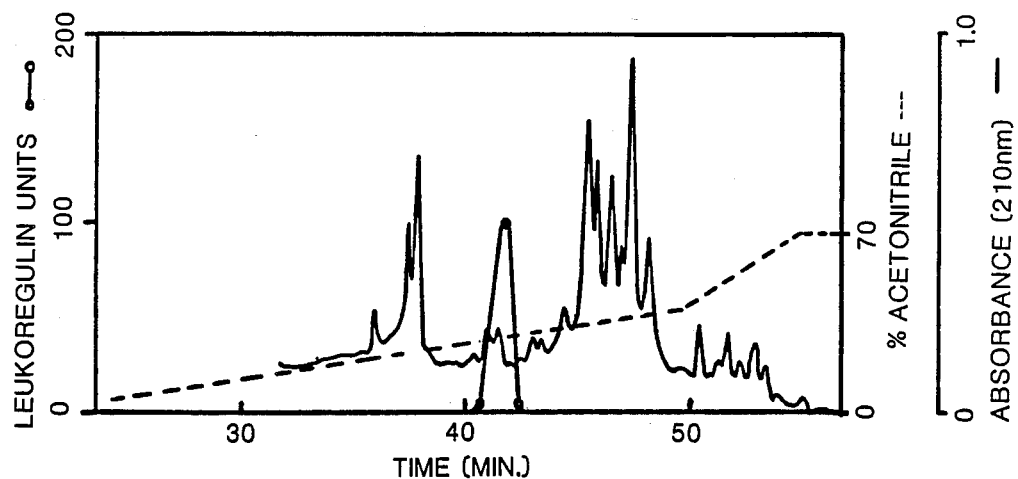
Figure 13B:
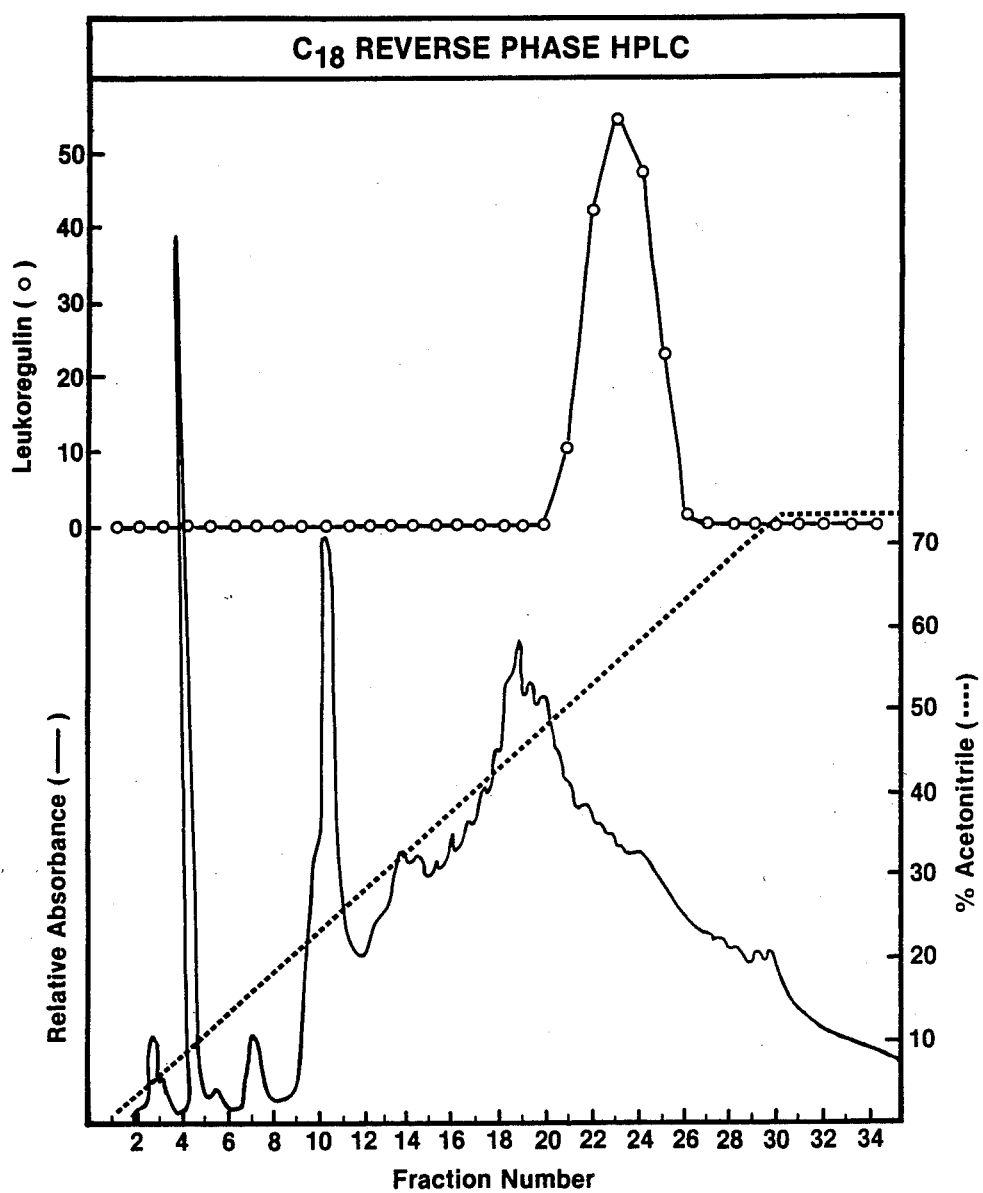

Leukoregulin partially purified by Blue A Agarose, Phenyl Sepharose and DEAE anion exchange chromatography was separated on either a $C_4$ (FIG. 13A) or a $C_{18}$ (FIG. 13B) reverse phase HPLC column. Leukoregulin bound to columns equilibrated in 90% by weight $H_2O$, 0.1% trifluoroacetic acid (TFA): 10% acetonitrile, 0.1% TFA, and eluted at a 37% or 47% acetonitrile concentration from the $C_4$ or $C_{18}$ columns, respectively. A linear gradient of 0–60% acetonitrile in 0.1% trifluoroacetic acid (TFA) was run at a flow rate of 1 to 2 ml/min., depending on column size. Both analytical and preparative columns yielded the same result. Fractions were rotary evaporated to a volume of 0.1 ml to remove acetonitrile and TFA before bioassay.

Table 1

The optimal conditions for leukoregulin production by normal human peripheral blood leukocytes or by human B cell lines formed after hybridization with a murine myeloma or spontaneously transformed in culture was determined. Maximum levels of leukoregulin produced by peripheral blood leukocytes was found when these cells were cultured for 48 hrs. in the presence of 5 μg PHA/ml of medium. Continuous human B cell lines or human B-mouse myeloma heterohybridomas produced leukoregulin constitutively over a three-day period when cultured in serum free RPMI-1640 medium. The addition of 100 μg tetradecanoyl phobol acetate/ml of medium enhanced leukoregulin production three-fold.

Table 2

Evidence for the presence of a unique anti-tumor lymphokine distinct from lymphotoxin was shown when the relative proportions of lymphotoxin (alpha L929 cytolytic activity) and human tumor cell cytostatic activity in lymphokine preparations from 6 different individuals were compared. Murine tumor cell cytolytic activity and human tumor cell cytostatic activity varied independently in the preparations, indicating that the two biological activities were mediated by distinctly different entities. Concentrated lymphokines from three individuals' leukocytes that were not stimulated with PHA or had PHA added for the last half of culture did not lyse any tumor cells and had no growth inhibitory activity. However, when the same leukocytes were stimulated with PHA for 24 hours they secreted significant amounts of lytic and growth inhibitory activities. Thus, the antitumor cell activities were not due to PHA, buffer, or a depletion of medium nutrients by the 24-hour cultured cells.

Table 3

Additional support for the existence of a novel lymphokine, hereafter referred to as leukoregulin, distinct from lymphotoxin was provided by examining the susceptibility of the cytolytic and tumor cell growth inhibitory lymphokine activities to neuraminidase and protease digestion. Human cytolytic lymphokine activity for alpha L929 cells (lymphotoxin) was diminished 49 and 92% by 0.2 and 0.4 units of neuraminidase without any significant inhibition of the lymphokine tumor cell growth inhibitory (leukoregulin) activity. Neuraminidase digestion in the presence of 10 mM sialic acid had no effect on either activity, ruling out the possibility of the effect on lymphotoxin being caused by contaminating proteases in the neuraminidase. Alternatively, both lymphotoxin and leukoregulin activities were inhibited by proteases, although to differing degrees. Six units of pronase completely destroyed all of the lymphotoxin activity while 52% of the leukoregulin activity remained in the sample. Thus, pronase digestion rendered an active human leukoregulin sample lymphotoxin free.

Syrian golden hamster lymphotoxin preparations also contained a leukoregulin type of activity for hamster tumor cells, and an anticarcinogenic activity (24). The anticarcingenic activity has not been measured in human lymphokine preparations due to the unavailability of a quantitative human cell transformation assay compared to that in hamsters (4). We sought to determine whether hamster lymphotoxin and leukoregulin activities could be separated based on their susceptibility to neuraminidase and protease digestion as were human lymphotoxin and leukoregulin. We also determined whether the anticarcinogenic activity co-purified with leukoregulin, to assess if hamster anticarcinogenic activity and leukoregulin are identical and therefore possibly one and the same in humans. As with human lymphotoxin, hamster lymphotoxin was degraded by neuraminidase and trypsin. The anticarcinogenic activity for hamster cells exposed to carcinogen and cytostatic activity directed towards hamster tumor cells, as for human leukoregulin, was not degraded by neuraminidase but was diminished by 42% by trypsin demonstrating a parallel differential susceptibility of leukoregulin and lymphotoxin to neuraminidase and protease digestion in the two species.

Table 4

A two-step fractionation procedure based on HPLC molecular size exclusion chromatography and isoelectric focusing was performed to determine whether the anti-cancer activity of human leukoregulin was separable and distinct from several other lymphokines and monokines. As predicted from the previous data, lymphotoxin activity was found in the high (45,000–74,000), middle (30,000–38,000) and low (17,000–20,000) molecular weight fractions and was enriched in the pH 6.0–6.8 fraction after focusing. Leukoregulin was present only in the high molecular weight material and was separated into two species with isoelectric pH's at 4.2–5.6 and 7.1–8.4. Although the leukoregulin enriched fractions contained some lymphotoxin activity, fractions 1 and 3 contained greater than 170 lymphotoxin units but no leukoregulin activity. Therefore, a lymphotoxin activity derived from stimulated human PBL can be separated from leukoregulin. The low molecular weight fraction contained all of the interleukin 1 and interleukin 2 and the majority of the interferon activities. No macrophage activating activity was detected in any fraction. All of the fractions also contained endotoxin. The amount of endotoxin did not correlate with the leukoregulin activity. Further evidence indicating that endotoxin does not mediate leukoregulin acitivity was that the addition of up to 20 ng/ml of lipopolysaccharide serotypes 055:B5 and 0111.B4 did not inhibit the growth of K562 cells.

Table 5

As the leukoregulin enriched fractions contained low levels of interferon an additional experiment was performed to determine to what extent interferon might contribute to the inhibition of tumor cell growth. Gamma interferon from one source (ML) neither lysed alpha L929 cells nor inhibited the growth of human K562 tumor cells. Gamma interferon from another source (FL) contained 2000 lymphotoxin units/ml but did not contain leukoregulin activity. Alpha interferon contained neither lymphotoxin nor leukoregulin. Leukoregulin activity therefore is not mediated by alpha or gamma interferon nor is it a result of the synergistic action of lymphotoxin and gamma interferon.

Table 6

Unfractioned lymphokine preparations contain an activity which enhances the susceptibility of tumor cells to NK-mediated cytotoxicity. The relationship of the target cell sensitizing activity to leukoregulin and to lymphotoxin was examined following HPLC and isoelectric focusing sequential fractionation of human lymphokine. Leukoregulin enriched fractions contained significant tumor cell NK-cytotoxicity enhancing activity. Fractions enriched in lymphotoxin and those containing the lower molecular weight lymphokines such as interferon did not enhance the susceptibility of K562 leukemia cells to NK-mediated cytotoxicity. Thus NK enhancing activity copurifies with or is identical to leukoregulin.

Table 7

A panel of human tumor and normal cells were examined for their susceptibility to leukoregulin. Gastrointestinal carcinomas as a group were found to be highly sensitive to leukoregulin. Leukoregulin did not affect the growth of either the normal colonic mucosal cells or the skin fibroblasts.

Table 8

Quantitation of the binding of monoclonal antibodies directed towards the leukoregulin cell surface receptor is predictive of the relative susceptibility of the cell to the growth inhibitory effects of leukoregulin. Anti-leukoregulin receptor antibodies bound signficantly to 15 to 23% of HT-29 cells while binding only to 2% of the ten fold less responsive K562 cells in this indirect immunofluorescent flow cytometric assay.

Table 9

In order to determine the potential in vivo effectiveness of leukoregulin on human cancers, freshly dissociated colon tumor cells were prepared and cultured in semi-solid agar medium containing leukoregulin. Colon cancer was targeted for evaluation because of the high susceptibility of the colon cancer cell lines to leukoregulin. Tumor cells from all four patients tested were growth inhibited in a dose dependent manner to leukoregulin, although to varying degrees. One patient's cells were inhibited 98% by 50 units of leukoregulin while another patient's were inhibited 42% with 4,000 units of leukoregulin. This suggests that leukoregulin has the potential to control the growth of human colon cancers.

Table 10

Growth inhibition of freshly dissociated human tumor cells derived from carcinoma and sarcoma origins by exposure to leukoregulin is demonstrated. Using a clonogenic type of assay where cell growth is measured in semi-solid agar medium, leukoregulin inhibited growth from 29 to 94%. These assays are equivalent to similar types of in vitro studies which measured the antiproliferative activity reported for various natural and recombinant interferons and standard cytotoxic agents, and which established the reliability of in vitro tumor cell assays for predicting a clinical anti-tumor response to these agents, by Salmon, S. E., *Cloning of Human Tumor Stem Cells* (N.Y.: Liss, 1980); Salmon, S. E., *Cancer Achievements, Challenges, and Prospects for the 1980's* (J. H. Burchenal et al, eds., N.Y.: Grune and Stratton, 1980); van Hoff et al, *Cancer Res.* 43, 1926–1931 (1983) and Alonso, K., *Cancer* 54, 2475–2479 (1984).

Table 11

Human colon adenocarcinoma HT-29 cells were implanted intrasplenically into nude mice to establish tumors. Mice administered intravenous leukoregulin showed tumor growth inhibition and, in those animals in which tumors became established, a dramatic reduction in tumor burden (84% reduction) was observed.

Table 12 and 12A

Leukoregulin can be concentrated and partially purified from PHA-induced leukocyte culture supernatants by Cibacron Blue A chromatography. Culture supernatants were eluted through a column containing Cibacron Blue Agarose equilibrated with 20 mM tris·HCl, pH 7.4 at 4° C. Leukoregulin was eluted with 1M KCl in 20 mM tris·HCl, pH 7.4.

Table 13

Phenyl-Sepharose CL-4B Chromatography

Leukoregulin bound to Phenyl-Sepharose CL-4B TM, Pharmacia, New Brunswick, N.J. at a 1.5M ammonium sulfate concentration and was eluted completely with 20 mM tris·HCl, pH 7.4 at 4° C.

Table 14

Ammonium Sulfate Precipitation

Leukoregulin precipitated upon addition of 75% ammonium sulfate. The precipitate containing active leukoregulin was solubilized by addition of 20 mM tris·HCl, pH 7.4.

Table 15 pH Stability

Leukoregulin activity is stable over a pH range of 2–8 but was inactivated at pH 10.

REFERENCES

1. Aggarwal, B. B., Moffat, B., and Harkins, R. N., "Human lymphotoxin: production by a lymphoblastoid cell line, purification and initial characterization", *J. Biol. Chem.*, 259:686–691, 1984.

2. Brouty-Boye, P. "Inhibitory effects of interferon on cell multiplication", *Lymphokine Reports*, 1:99–112, 1980.

3. Brown, R. L., Griffith, R. L., Neubauer, R. H., and Rabin, H., "The effect of T-cell growth factor on the cell cycle of primate T cells", *J. Immunol.*, 129:1849–1853, 1982.

4. DiPaolo, J. A., "Relative difficulties in transforming human and animal cells in vitro", *J. Natl. Cancer Inst.*, 70:3–8, 1983.

5. Dolbeare, F. A., and Smith, R. E., "Flow cytoenzymology: Rapid enzyme analysis of single cells", In, M. R. Melamid, P. F. Mullaney, and M. L. Mindelsohn (eds.), *Flow Cytometry and Sorting*, pp. 317–334, N.Y., John Wiley & Sons, 1979.

6. Evans, C. H., and DiPaolo, J. A., "Lymphotoxin: an anticarcinogenic lymphokine as measured by inhibition of chemical carcinogen or ultraviolet-irradiation-induced transformation of Syrian hamster cells", *Int. J. Cancer*, 27:45–49, 1981.

7. Evans, C. H. and Heinbaugh, J. A., "Lymphotoxin cytotoxicity, a combination of cytolytic and cytostatic cellular responses", *Immunopharmacology*, 3:347–359, 1981.

8. Evans, C. H., Heinbaugh, J. A., and DiPaolo, J. A., "Comparative effectiveness of lymphotoxin anticarcinogenic and tumor cell growth inhibitory activities", *Cell. Immunol.*, 76:295–303, 1983.

9. Granger, G. A., and Kolb, W. P., "Lymphocyte in vitro cytotoxicity: mechanisms of immune and non-immune small lymphocyte mediated target L cell destruction", *J. Immunol.*, 101:111–116, 1968.

10. Haspel, M. V., et al., *Science* 220:304–306, 1983.

11. Hoover, H. C., et al, *Cancer Res.*, Apr., 1984.

12. Kern, et al., *Int. J. Cancer*, 30:725–729, 1982.

13. Khan, A., et al., In *Human Lymphokines*, pp. 621–629, Academic Press, N.Y., 1982.

14. Kleinerman, E. S., Schroit, A. J., Fogler, W. E., and Fidler, I. J., "Tumoricidal activation of human monocyte activity in vitro by free and liposome encapsulated human lymphokines", *J. Clin. Invest.,* 72:304–315, 1983.

15. Laemmli, V., *Nature,* 227:680–685, 1970.

16. Lambin, P., and Fine, J. M., *Anal. Biochem.,* 98:160–168, 1979.

17. McConahey, P. J., and Dixon, F. J., *Int. Arch. Allergy Appl. Immunol.,* 29:185–189, 1966.

18. Mizel, S. B., Oppenheim, J. J., and Rosenstreich, D. L., "characterization of lymphocyte-activating factor produced by the macrophage cell line P388D1. I. Enhancement of LAF production by activated T lymphocytes", *J. Immunol.,* 120:1497–1505, 1978.

19. Papermaster, B. W., et al., In *Lymphokines and Thymic Hormones,* Academic Press, N.Y., pp. 789–799.

20. Penn, I., "Depressed Immunity and the Development of Cancer", *Clinical Experimental Immunology,* 46:459, 1981.

21. Pross, H. F., Baines, M. G., Rubin, P., Shragge, P., and Patterson, M. S., "Spontaneous human lymphocyte-mediated cytotoxicity against tumor target cells. IX. The quantitation of natural killer cell activity", *J. Clin. Immunol.,* 1:51–63, 1981.

22. Rabin, H., Hopkins, R. F., Ruscetti, F. W., Neubauer, R. H., Brown, R. L., and Kawakami, T. G., "Spontaneous release of a factor from a continuous line of primate tumor T cells", *J. Immunol.,* 127:1852–1856, 1981.

23. Ransom, J. H. and Evans, C. H., "Lymphotoxin enhances the susceptibility of neoplastic and preneoplastic cells to natural killer cell mediated destruction", *Int. J. Cancer,* 29:451–458, 1982.

is specific for natural killer cells but not for macrophages", *Int. J. Cancer,* 32:93–97, 1983.

28. Ransom, J. H., Rundell, J. O., Heinbaugh, J. A., and Evans, C. H., "Biological and physiocochemical characterization of keyhole limpet hemocyanin-induced guinea pig lymphotoxin", *Cell. Immunol.,* 67:1–13, 1982.

29. Remold, H. G., and Mednis, A. D., "Two migration inhibitory factors differ in density and susceptibility to neuraminidase and proteinases", *J. Immunol.,* 122:1920–1925, 1978.

30. Rosenberg, S. A., Henrichon, M. Coyne, J. A., and David, J. A., "In vitro studies of LT produced in response to antigen stimulation of lymphocytes", *J. Immunol,* 6:1623–1629, 1973.

31. Sawada, J., Shiori-Nakano, K., Osawa, T., "Cytotoxic activity of purified guinea pig lymphotoxin against various cell lines", *Jpn. J. Exp. Med.,* 4:263–271, 1976.

32. Trinchieri, G., DeMarchi, M., Mayer, W., Savi, M., and Ceppelline, R., "Lymphocyte antibody lymphocytolytic interaction (LALI) with special emphasis on HLA", *Transplant. Proc.,* 5:1631–1646, 1973.

33. Trinchieri, G., and Santoli, D., "Anti-viral activity induced by culturing lymphocytes with tumor-derived or virus-transformed cells", *J. Exp. Med.,* 147:1314–1333, 1978.

34. Williamson, B. D., Carswell, E. A., Rubin, B. Y., Prendergast, J. S., and Old, L. J., "Human tumor necrosis factor produced by human B-cell lines: synergistic cytotoxic interaction with human interferon", *Proc. Natl. Acad. Sci.,* 80:5397–5401, 1983.

TABLE 1

| Conditions for Optimal Leukoregulin Production | | | | |
|---|---|---|---|---|
| Peripheral Blood Leukocytes | | Human B Cell Lines | | |
| Incubation Conditions[a] | Leukoregulin Produced (Units/ml) | Cell Line | Incubation Conditions[b] | Leukoregulin Produced (Units/ml) |
| 24 hr. culture with: | | | | |
| 10 μg PHA/ml | 8 | 6a3-1[c] | RPMI-1640 10% FBS | 12 |
| 5 μg PHA/ml | 45 | 1688[d] | RPMI-1640 | 0.5 |
| 1 μg PHA/ml | 0.1 | 1688 | RPMI-1640 with 10 μg TPA/ml | 1.5 |
| 10 μg PHA/ml with: | | | | |
| 24 hr. culture | 8 | | | |
| 48 hr. culture | 205 | | | |
| 72 hr. culture | 120 | | | |

[a] $10^6$ PBL/ml RPMI 1640.
[b] $2 \times 10^5$ cells/ml medium, 3 days at 37° C.
[c] Human-mouse heterohybridoma.
[d] Human transformed diploid B cell.

24. Ransom, J. H. and Evans, C. H., "Molecular and biological characterization of Syrian hamster lymphotoxin's anticarcinogenic and tumor cell growth inhibitory activities", *Cancer Res.,* 43:5222–5227, 1983.

25. Ransom, J. H., Evans, C. H., and DiPaolo, J. A., "Lymphotoxin prevention of diethylnitrosamine carcinogenesis in vivo", *J. Natl. Cancer Inst.,* 69:741–744, 1982.

26. Ransom, J. H., Evans, C. H., Jones, A. E., Zoon, R. A., DiPaolo, J. A., "Control of the carcinogenic potential of [99m]technectium by the immunologic hormone lymphotoxin", *Cancer Immunol. Immunother.,* 15:126–130, 1983.

27. Ransom, J. H., Pintus, C., and Evans, J. H. "Lymphotoxin amplification of tumor cell growth inhibition

TABLE 2

Relative Amounts of Cytolytic and Cytostatic Activities in Human Lymphokine Preparations from Different Individuals

| Preparation | Alpha L929 Cytolytic Units/ml | K562 Cytostatic Units/ml | Ratio[a] |
|---|---|---|---|
| HU-4 | 1,600 | 95 | 17 |
| HU-8 | 10,000 | 8 | 1,250 |
| HU-11 | 970 | 42 | 23 |
| HU-12 | 5,000 | 4 | 1,250 |
| HU-13 | 1,500 | 93 | 16 |
| HU-17 | 5,400 | 20 | 270 |

[a] Ratio of cytolytic units:cytostatic units

TABLE 3
Differential Sensitivity of Lymphotoxin and Leukoregulin Activities to Neuraminidase and Protease Digestion

| | Human Lymphokine | | | | | Syrian Hamster Lymphokine | | |
|---|---|---|---|---|---|---|---|---|
| | Experiment I | | Experiment II | | | | | |
| Treatment[a] | Alpha L929 Cytolytic Units/ml | K562 Cytostatic Units/ml | Alpha L929 Cytolytic Units/ml | K562 Cytostatic Units/ml | 2650 Cytostatic Units/ml | Alpha L929 Cytolytic Units/ml | 7997 Cytostatic Units/ml | Anticarcinogenic Units/ml |
| Medium | 358 | 10 | 5400 | 20 | 18 | 430 | 24 | 158 |
| 0.2 units VCN | 181 (49)[b] | 10 (0) | | | | 132 (70)[b] | 23 (5) | 150 (5) |
| 0.4 units VCN | | | 450 (92) | 19 (5) | 17 (6) | | | |
| PBS | 560 | 25 | | | | 2468 | 60 | 681 |
| 32 units trypsin | 25 (96) | 17 (32) | | | | 471 (81) | 27 (42) | 392 (42) |
| 6 units chymotrypsin | 4 (99) | 16 (36) | | | | | | |
| 6 units pronase | 0 (100) | 13 (48) | | | | | | |

[a] One hour at 37° C.
[b] Percent inhibition in parenthesis.

TABLE 4
Human Lymphokine Activities after Fractionation By HPLC and Isoelectric Focusing[a]

| Molecular Weight | 45,000–74,000 | | | 30,000–38,000 | | | 17,000–22,000 |
|---|---|---|---|---|---|---|---|
| Isoelectric pH | 4.2–5.6 | 6.0–6.8 | 7.1–8.4 | 4.2–5.6 | 6.0–6.8 | 7.1–8.4 | not focused |
| Fraction No. | 7 | 6 | 5 | 4 | 3 | 2 | 1 |
| Activity[b] | | | | | | | |
| Lymphotoxin[c] | 16 | 163 | 25 | 5 | 176 | 25 | 205 |
| Leukoregulin: | | | | | | | |
| on K562[d] | 26 | 2 | 12 | 0 | 0 | 0 | 0 |
| on 2650[e] | 13 | 3 | 37 | 0 | 0 | 0 | 0 |
| Interleukin-1 | 0 | 0 | 0 | 0 | 0 | 0 | 160 |
| Interleukin-2 | 0 | 0 | 0 | 0 | 0 | 0 | 6000 |
| Macrophage Migration Inhibition | 640 | 20 | 80 | 0 | 0 | 0 | 0 |
| Macrophage Activation | 0 | 0 | 0 | 0 | 0 | 0 | 0 |
| Endotoxin[f] | 20 | 8 | 10 | 14 | 11 | 10 | 5 |
| Interferon | 25 | 10 | 10 | 0 | 5 | 5 | 250 |

[a] Two ml of human lymphokine preparation containing 750 lymphotoxin units and 55 K562 cytostatic leukoregulin units were separated by gel permeation chromatography into fractions with molecular weights of 45,000–74,000, 30,000–38,000 and 17,000 to 22,000. The 17,000–22,000 fraction was held at 4° C. while the two higher molecular weight fractions were separated further by isoelectric focusing into fractions with pH's of 7.2–8.4, 6.1–6.9, and 4.2–5.6. The fraction pools after focusing were dialyzed against PBS-PEG and filter sterilized before assay.
[b] All activities are expressed in units/ml.
[c] Lysis of alpha L929 cells.
[d] Growth inhibitory units.
[e] Lytic units.
[f] Ng/ml.

TABLE 5
Determination of Interferon Antitumor Cell Activity

| Human Interferon Type & Source | Antiviral Units/ml | Lymphotoxin[a] Units/ml | Leukoregulin[b] Units/ml |
|---|---|---|---|
| gamma-(FL) | $5 \times 10^5$/ml | 2000 | 0 |
| gamma-(ML) | $5 \times 10^5$/ml | 0 | 0 |
| alpha-(S) | 1000/ml | 0 | 0 |

[a] Lysis of alpha L929 cells.
[b] Growth inhibition of K562 cells.

TABLE 6
Molecular Characterization of Tumor Cell NK Cytotoxicity Enhancing Activity[a]

| Molecular Weight | 45,000–74,000 | | | 17,000–22,000 | NK |
|---|---|---|---|---|---|
| Isoelectric pH | 4.5–5.5 | 6.0–6.7 | 7.4–8.5 | Not Focused | Media Control |
| Lymphotoxin[b] | 0 | 151 | 0 | 70 | |
| Leukoregulin[c] | 8 | 1 | 3 | 0 | |
| NK Lytic Units[d] per $10^4$ cells | 548[f] | 356 | 447[f] | 253 | 276 |
| NK enhancement[e] | 2.0 | 1.3 | 1.7 | 0.9 | |

[a] Two ml of a human lymphokine preparation were separated by molecular sieving HPLC chromatography into fractions with molecular weights of 45,000–74,000 and 17,000–22,000. The higher molecular weight fraction was separated by isoelectric focusing into fractions with isoelectric pH's of 4.5–5.5, 6.0–6.7 and 7.4–8.5. All fraction pools were dialyzed against PBS-PEG and filter sterilized before assay.
[b] Lysis of alpha L929 cells in units/ml.
[c] Growth inhibition of K562 cells in units/ml.
[d] K562 cells in 1 ml of a test fraction diluted 1:5 or media were incubated 1 hour then assayed in a 4 hour $^{51}$Cr release assay with NK cells.
[e] The ratio of the NK lytic units/$10^4$ cells of the treatment group to that of the NK media control.
[f] Statistically significantly different than the control ($p < 0.05$) by Student's t-test.

TABLE 7
Relative Susceptibilities of Human Tumor and Normal Cells to Leukoregulin

| Cell | Type | Number of units[a] causing a 50% inhibition of cell growth | | Number of units causing 50% cytolysis | Population doubling time (hours) |
|---|---|---|---|---|---|
| | | unfractionated | purified[b] | | |
| Gastrointestinal carcinomas | | | | | |
| HT-29 | colon | 1.0 | 1.0 | 32 | 31 |
| Widr | colon | 1.6 | 1.7 | 52 | 40 |
| SW-480 | colon | 1.2 | 2.2 | c | 23 |
| SW-948 | colon | 2.9 | | | |
| HUTU-80 | duodenum | 6.0 | 2.2 | | |
| GW-39 | colon | | 1.5 | | 20 |
| LS-174 | colon | | 13. | | 26 |
| 1463 | rectum | 84 | | | |
| LoVo | colon | 120 | | | 32 |
| CaCo | colon | 730 | | | 45 |
| Bladder carcinomas | | | | | |
| HT-1376 | | | 3.4 | | 35 |
| RT-4 | transitional cell | 20 | | | 40 |

TABLE 7-continued

Relative Susceptibilities of Human Tumor and Normal Cells to Leukoregulin

| Cell | Type | Number of units[a] causing a 50% inhibition of cell growth unfractionated | purified[b] | Number of units causing 50% cytolysis | Population doubling time (hours) |
|---|---|---|---|---|---|
| J-82 | transitional cell | 66 | 390 | | |
| T-24 | transitional cell | 310 | | | 33 |
| SCABER | squamous | No effect | | | |
| Other cancers | | | | | |
| 2650 | Nasal carcinoma | 1.4 | 0.6 | 3 | 21 |
| KB | Mouth Epidermoid | 8 | | | |
| HeLa | Cervix epithelial cancer | 8 | | | |
| K562 | Erythroleukemia | 10 | | d | |
| Hep-2 | Larynx, epidermoid | 50 | | | |
| Normal cells | | | | | |
| Bell | Colonic mucosal cells | No effect | No effect | | |
| 1467 | Adult skin fibroblast | No effect | No effect | | |
| 1505 | Adult skin fibroblast | No effect | No effect | | |
| 1537 | Adult skin fibroblast | No effect | No effect | | |

[a]One unit by definition is the amount which causes a 50% growth inhibition of $2 \times 10^3$ HT-29 cells after 72 hours of culture
[b]Leukoregulin was purified by sequential HPLC-gel filtration, then ion exchange chromatography and linear gradient polyacrylamide gel electrophoresis.
[c]Maximally 14% cytolysis occured with 450 units/ml.
[d]Maximally 25% cytolysis occured with 700 units/ml.

TABLE 8

Flow Cytometric Analysis of the Binding of Monoclonal Antibody to the Leukoregulin Cell Surface Receptor

| Monoclonal Antibody | Percent Positive Cells | |
|---|---|---|
| | HT-29 | K562 |
| LrR-MP28 | 23 | 2 |
| LrR-M2 | 15 | 2 |

TABLE 9

Effect of Leukoregulin on Freshly Excised Human Colon Tumor Cells Growing in Agar

| Patient Name or Number | Colonies per[a] well without leukoregulin ± SE | % inhibition (leukoregulin units/ml)[b] | | |
|---|---|---|---|---|
| Cohen | 22 ± 6 | 98 (50) | 68 (5) | 36 (0.5) |
| 84-2027 | 72 ± 4 | 42 (4000) | 28 (400) | 3 (40) |
| 84-1991 | 44 ± 6 | 38 (4000) | 0 (400) | 0 (40) |
| 845-1752 | 60 ± 4 | 25 (375) | 13 (38) | 0 (4) |

[a]$2 \times 10^5$ cells seeded in 1 ml wells.
[b]One leukoregulin unit caused a 50% inhibition of the growth of $2 \times 10^3$ HT-29 cells in 3 days.

TABLE 10

AGAR CLONOGENIC ASSAY RESULTS

| Tumor Type | Percent Inhibition of Colony Formation[a] |
|---|---|
| Colon Carcinomas | |
| THO | 92 |
| ATK | 91 |
| EPP | 91 |
| BLU | 40 |
| Lung Carcinomas | |
| LS-1 | 78 |
| LX-1 | 53 |
| LS-16 | 74 |
| LS-13 | 34 |
| Mammary Carcinoma | |
| MX-1 | 29 |
| Sarcoma | |
| BRI | 94 |

[a]Collagenase dissociated human tumor cells propagated from primary tumors in nude mice were suspended in 0.15% agar, containing medium or 25 units of leukoregulin. After 2 weeks incubation at 37° C., the resultant tumor colonies >2 mm in diamter were counted. The percent inhibition is the percent reduction in colonies formed by cells plated in leukoregulin compared to media alone.

TABLE 11

LEUKOREGULIN THERAPY OF HT-29 INJECTED INTRASPLENICALLY INTO ATHYMIC (NU/NU) MICE[a]

| TUMOR SITE | CONTROL | TREATED | % INHIBITION |
|---|---|---|---|
| SPLEEN | | | |
| INCIDENCE | 12/14 | 4/10 | |
| TUMOR BURDEN (gm) | 1.08 | 0.17 | 84 |
| LIVER | | | |
| INCIDENCE | 2/14 | 0/10 | |
| LUNG | | | |
| INCIDENCE | 4/14 | 1/10 | |
| MICE WEIGHT (gm) | 22.5 | 22.3 | |

[a]Mice were injected intrasplenically with $2 \times 10$ HT-29 human colon adenocarcinoma cells. This tumor grows as a primary in the spleen and also forms metastases in the liver and lungs. Mice were injected intravenously 3 times a week with a purified leukoregulin preparation for a total dosage of 6,000 units. Control mice were injected with PBS using the same schedule. After 8 weeks mice were euthanized and the tumor burden assessed.

TABLE 12

BLUE A AGAROSE PURIFICATION OF LEUKOREGULIN[a]

| Sample | LR Units | |
|---|---|---|
| Starting Material | 2575 | |
| Flow Through (Non bound) | 0 | |
| 0.1 M KCl | 37 | |
| 0.25 M KCl | 269 | |
| 0.50 M KCl | 450 | |
| 0.75 M KCl | 555 | |
| 1.0 M KCl | 355 | |
| 1.5 M KCl | 90 | |
| Total Recovery | 1756 | 68% |

[a]A 100 ml crude supernatant was eluted on 30 ml of Cibacron Blue A Agarose. Sequential elution with increasing KCl concentrations was performed step-wise with 50 ml of each concentration.

TABLE 12A

BLUE A AGAROSE CHROMATOGRAPHY RESULTS SUMMARY

| Preparation Number | Starting Preparation[a] | | | After Blue A | | | % Yield[d] | Fold Purification[d] |
|---|---|---|---|---|---|---|---|---|
| | Total Units | Total Protein[b] | Specific Activity[c] | Total Units | Total Protein | Specific Activity | | |
| HUF42 | 48,000 | 317 | 151 | 19,000 | 29 | 655 | 40 | 4.3 |
| HUF44-1 | 138,600 | 504 | 275 | 128,000 | 10 | 12,800 | 92 | 25 |
| HUF44-2 | 57,200 | 380 | 150 | 56.077 | 115 | 486 | 98 | 3.2 |
| HUF45 | 172,200 | 1033 | 167 | 52,000 | 167 | 311 | 30 | 1.9 |
| HUF47 | 517,661 | 682 | 759 | 226,000 | | | 44 | |
| HUF48 | 265,320 | 281 | 943 | 88,400 | | | 33 | |
| HUF49 | 285,390 | 326 | 875 | 57,410 | 18.9 | 3,042 | 20 | 3.5 |
| HUF50 | 104,369 | 573 | 182 | 16,368 | 36.3 | 451 | 16 | 2.5 |
| Average | | | 438 | | | 2,958 | 47 | 6.7 |

[a]Crude culture supernatant.
[b]mg
[c]units/mg
[d]Relative to starting preparation.

TABLE 13

PHENYL-SEPHAROSE CHROMATOGRAPHY OF LEUKOREGULIN[a]

| Sample | Leukoregulin Units | % Recovery |
|---|---|---|
| Starting Material | 3555 | |
| Non Bound | 0 | |
| Bound and Eluted with 20 mM Tris | 2846 | 70% |

[a]Leukoregulin in 1 M KCl, pooled after purification on a Cibacron Blue A Agarose Column as described in Table 12, was adjusted to a 1.5 M concentration of ammonium sulfate. Leukoregulin was eluted on and bound to a 30 ml phenyl-Sepharose column equilibrated with 1 M KCl—1.5 M $(NH_4)_2SO_4$. Leukoregulin eluted from this column by the addition of 200 ml of 20 mM Tris-HCL pH 7.4. The column flow rate was 8 ml/min.

TABLE 14

AMMONIUM SULFATE PRECIPITATION OF LEUKOREGULIN[a]

| Sample | Leukoregulin Units | % Recovery |
|---|---|---|
| Starting Material | 4285 | |
| 25% Ammonium Sulfate | 24 | 0.6 |
| 50% Ammonium Sulfate | 53 | 1.0 |
| 75% Ammonium Sulfate | 2720 | 63.0 |

[a]Leukoregulin in 1 M KCl pooled after purification on a Cibacron Blue A Agarose Column as described in Table 12 was adjusted to 25%, 50%, or 75% concentration with solid ammonium sulfate. The mixture was stirred 2 hr. at 4° C., centrifuged at 10,000 × g, and the pellet resuspended and dialyzed versus 20 mM tris-HCl pH 7.4.

TABLE 15 pH STABILITY OF LEUKOREGULIN[a]

| Treatment | LR units/ml | % of pH 7.2 |
|---|---|---|
| pH 2.0 | 25.2 | 62% |
| pH 3.0 | 23.5 | 58% |
| pH 4.0 | 23.0 | 57% |
| pH 5.0 | 24.9 | 61% |
| pH 6.0 | 32.0 | 79% |
| pH 7.2 | 40.5 | |
| pH 8.0 | 31.0 | 77% |
| pH 10.0 | 9.4 | 23% |

[a]A partially purified leukoregulin sample was adjusted to the appropriate pH with HCl or NaOH, held at room temperature 2 hrs., then neutralized. The pH 7.2 sample was maintained without pH adjustment as a control.

The above-described embodiments are provided to illustrate the present invention but are not intended to be limiting, as the scope of the invention is defined by the claims that follow and is intended to include all equivalents, variations, and improvements, modifications, and mutations thereof.

What is claimed is:

1. The isolated and concentrated lymphokine, leukoregulin, which has the ability to directly lyse human HT-29 and RPMI 2650 tumor cells but not lyse murine αL929 cells, to suppress K562 human tumor cell proliferation, and to enhance the susceptibility of K562 tumor cells to NK cell mediated lysis but altering K562 tumor cell surface conformation and permeability, which is not neutralized by antisera to lymphotoxin, tumor necrosis factor, interferon or cytolysin, said lymphokine having a molecular weight of about 120,000 to 140,000 as determined by native gradient polyacrylamide gel electrophoresis, 50,000 to 70,000 by gel permeation chromatography, and isoelectric focusing points in the pH ranges of 4.8 to 5.5 or 7.5 to 8.3 and subunits thereof having the same biological activity.

2. A biologically active composition of matter comprising an effective amount of leukoregulin and a pharmaceutically acceptable carrier.

3. The composition of matter recited in claim 2, comprising in addition one or more ingredients having supplemental or complementary biological activity.

* * * * *